US011518802B2

(12) United States Patent

Merino Pérez et al.

(10) Patent No.: US 11,518,802 B2
(45) Date of Patent: Dec. 6, 2022

(54) MONOCLONAL ANTIBODIES AGAINST BAMBI AND USE FOR THE TREATMENT OF INFLAMMATORY DISEASES

(71) Applicants: CONSEJO SUPERIOR DE INVESTIGACIONES CIENTIFICAS (CSIC), Madrid (ES); UNIVERSIDAD DE CANTABRIA, Santander (ES)

(72) Inventors: Jesús Merino Pérez, Santander (ES); Ramón Merino Pérez, Santander (ES)

(73) Assignees: CONSEJO SUPERIOR DE INVESTIGACIONES CIENTIFICAS (CSIC), Madrid (ES); UNIVERSIDAD DE CANTABRIA, Cantabria (ES)

( * ) Notice: Subject to any disclaimer, the term of this patent is extended or adjusted under 35 U.S.C. 154(b) by 687 days.

(21) Appl. No.: 15/780,800

(22) PCT Filed: Nov. 30, 2016

(86) PCT No.: PCT/ES2016/070852

§ 371 (c)(1),
(2) Date: Jul. 16, 2019

(87) PCT Pub. No.: WO2017/093589

PCT Pub. Date: Jun. 8, 2017

(65) Prior Publication Data

US 2019/0338019 A1 Nov. 7, 2019

(30) Foreign Application Priority Data

Dec. 3, 2015 (ES) ................................ P201531761

(51) Int. Cl.

| | |
|---|---|
| ***A61K 39/395*** | (2006.01) |
| ***C07K 16/22*** | (2006.01) |
| ***A61P 37/06*** | (2006.01) |
| ***A61P 19/02*** | (2006.01) |
| ***A61K 35/16*** | (2015.01) |

(52) U.S. Cl.

CPC .............. *C07K 16/22* (2013.01); *A61K 35/16* (2013.01); *A61K 39/3955* (2013.01); *A61P 19/02* (2018.01); *A61P 37/06* (2018.01); *C07K 2317/34* (2013.01)

(58) Field of Classification Search

CPC ............................ A61K 39/3955; C07K 16/22
See application file for complete search history.

(56) References Cited

U.S. PATENT DOCUMENTS

2007/0065446 A1* 3/2007 Akiyama ......... G01N 33/57438 424/155.1

FOREIGN PATENT DOCUMENTS

| | | |
|---|---|---|
| WO | WO2005054273 A2 | 6/2005 |
| WO | WO2007092939 A2 | 8/2007 |
| WO | WO2008094597 A2 | 8/2008 |
| WO | WO2010/108005 A2 | 9/2010 |
| WO | WO2014107165 A1 | 7/2014 |

OTHER PUBLICATIONS

Knappik et al., J. Mol. Biol., 2000, vol. 296(1):57-86.*
Nair et al.,2002, J. Immunol., vol. 168(5):2371-2382.*
Lu et al., J. Immunol., 2004, vol. 173(6):3972-3978.*
Khmaladze et al., "Mannan induces ROS-regulated, IL-17A-dependent psoriasis arthritis-like disease in mice", Proceedings of the National Academy of the Sciences of the United States of America, vol. 111, (35), Sep. 2, 2014, pp. E3669-E3678.
Aletaha et al., "2010 Rheumatoid arthritis classification criteria: an American College of Rheumatology/European League Against Rheumatism collaborative initiative", Arthritis and Rheumatism, vol. 62, No. 9, Sep. 2010, pp. 1580-1892.
Rudwaleit et al., "The Assessment of SpondyloArthritis international Society classifi cation criteria for peripheral spondyloarthritis and for spondyloarthritis in general", Annals of the Rheumatic Diseases, vol. 70, No. 1, Nov. 24, 2010, pp. 25-31.
Tan et al., "The 1982 Revised Criteria for the Classification of Systemic Lupus Erythematosus", Arthritis and Rheumatism, vol. 25, No. 11, Nov. 1982, pp. 1271-1277.
Xavier et al., "BAMBI Is Expressed in Endothelial Cells and Is Regulated by Lysosomal/Autolysosomal Degradation", PLOS One, vol. 5, Issue 9, e12995 Sep. 24, 2010.
Jorge Postigo Fernández, "BAMBI, Un Inhibidor De La Señalización De TGFβ, En La Actividad Biológica De Los Linfocitos T-CD4+", Doctoral Thesis, Universidad de Cantabria, Apr. 19, 2013.
Bennett et al., "The immune dysregulation, polyendocrinopathy, enteropathy, X-linked syndrome (IPEX) is caused by mutations of FOXP3", Nature Genetics, vol. 27, No. 1, Jan. 2001, pp. 20-21.
Iglesias et al., "p27$^{Kip1}$ Inhibits Systemic Autoimmunity Through the Control of Treg Cell Activity and Differentiation", Arthritis & Rheumatism vol. 65, No. 2, Feb. 2013, pp. 343-354.
International Search Report & Written Opinion of the International Searching Authority dated Mar. 3, 2017, for PCT application No. PCT/ES2016/070852.
Khattri et al., "An essential role for Scurfin in CD4+CD25+ T regulatory cells", Nature Immunology, Mar. 3, 2003, vol. 4, No. 4, pp. 337-342.
Kebir et al., "Human $T_H$17 lymphocytes promote blood-brain barrier disruption and central nervous system inflammation", Nature Medicine, Oct. 2007, vol. 13, No. 10, pp. 1173-1175.
Zhu et al., "Differentiation of Effector CD4 T Cell Populations*", Annual Review of Immunology, 2010, vol. 28, pp. 445-489.

(Continued)

*Primary Examiner* — Xiaozhen Xie

(74) *Attorney, Agent, or Firm* — Womble Bond Dickinson (US) LLP

(57) ABSTRACT

The invention relates to monoclonal antibodies, in particular against a peptide of the BAMBI protein, as well as the uses thereof and methods comprising same. Preferably, the antibodies are used for the treatment of autoimmune diseases.

7 Claims, 16 Drawing Sheets

Specification includes a Sequence Listing.

(56) References Cited

OTHER PUBLICATIONS

Rohn et al., "Vaccination against IL-17 suppresses autoimmune arthritis and encephalomyelitis", European Journal of Immunology, Nov. 2006. vol. 36,No. 11, pp. 2857-2867.

Shoenfeld et al. "The autoimmunologist: geoepidemiology, a new center of gravity, and prime time for autoimmunity", Aug. 12, 2008, Journal of Autoimmunity, vol. 31, pp. 325-330.

Zygmunt et al., "Chapter 5—T Helper Cell Differentiation: More than Just Cytokines", 2011 Advances in Immunology, vol. 109:159-196.

Tangye et al., "The good, the bad and the ugly—$T_{FH}$ cells in human health and disease", May 17, 2013, Nature Reviews: Immunology, vol. 13, pp. 412-426.

Yokoyama, W.M., et al., "Production of Monoclonal Antibodies", Current Protocols in Immunology, Oct. 2013, vol. 102, Issue 1, pp. 2.5.1-2.5.29.

Wang, Z., et al. "Recombinant Technology Universal PCR amplification of mouse immunoglobulin gene variable regions: the design of degenerate primers and an assessment of the effect of DNA polymerase 3' to 5' exonuclease activity", Journal of Immunological Methods, Jan. 13, 2000, vol. 233, pp. 167-177.

Wooley, PH., et al. "Type II Collagen-Induced Arthritis In Mice. IV. Variations in Immunogenetic Regulation Provide Evidence for Multiple Arthritogenic Epitopes on the Collagen Molecule.", Journal of Immunology, Oct. 1985, vol. 135, No. 4, pp. 2443-2451.

* cited by examiner

Fig. 1C

*mAb B101-37*

*Heavy chain: IgHV9-3/D1-3/J1*

CAGCTGGAGCAGTCAGGACCTGAGCTGAAGAGGCCTGGAGAGACAGTCAAGTTCTCCTGCAAGGCTTCTGGGT
ATCCCTTCACAAACTATGGAATGCACTGGGTGAAACAGGCTCCAGGAAAGGGTTTAAAGTGGATGGGCTGGATAA
ACACCCACACTGGAGAGCCAACATATGCTGATGACTTCAGGGGACGGTTTGCCTTCTCTTTGGAAACCTCTGCCA
GCACTGCCTATTTGCAGATCAACAACCTCAAAAATGAGGACACGGCTACATATTTCTGTGCAAGAGAGGGTTATTAT
AACTACGAAGGCTGGTACTTCGATGTCTGGGGCGCAGGGACCACGGTCACCGTCTCCTCAGCCAAAACGACACC
CCCATCTGTCTATAGATCTTCC

*Light chain: IgκV15-103/J5*

GGGAGCTCGACATTGTGCTGACCCAGTCTCCATCCAGTCTGTCTGCATCCCTTGGAGACACAATTACCATCACTTG
CCATGCCAGTCAGAACATTTATTTTTGGTTAAGTTGGTACCAGCAGAAACCAGGAAATATTCCTAAACTATTGATCTAT
AAGGCTTCCAACTTGCACACAGGCGTCCCATCAAGGTTTAGTGGCAGTGGATCTGGAACAGGTTTCACATTAACCA
TCAGCAGCCTGCAGCCTGAAGACATTGCCACTTACTACTGTCAACAGGGTCAAAGTTATCCGCTCACGTTCGGTGC
TGGGACCAAGCTGGAGCTGAAACGGGCTGATGCTGCACCAACTGTATCCGCATGCACC

*mAb B143-14*

*Heavy chain: IgHV1-55/D4-1/J2*

CTTCCGGAATTCCAAGTTCAGCTGGAGGAGTCAGGGGCTGAGCTTGTGAAGCCTGGGGCTTCAGTGAAGATGTCC
TGCAAGGCTTCTGGCTACACCTTCACCAGCTACTGGATAAACTGGGTGAAGCTGAGGCCTGGACAAGGCCTTGAGT
GGATTGGAGATATTTATCCTGGTAGTGGTAGTACTAACTACAATGAGAAGTTCAAGAGCAAGGCCACACTGACTGTAG
ACACATCCTCCAGCACAGCCTACATGCAACTCAGCAGCCTGACATCTGAGGACTCTGCGGTCTATTACTGTGCAACT
GGGTTTGACTACTGGGGCCAAGGCACCACTCTCACAGTCTCCTCAGAGAGTCAGTCCTTCCCAAATGTCAGATCTT
CC

*Light chain (κ): IgκV5-43/J1*

GGGAGCTCGACATTGTGCTCACCCAGTCTCCAGCCACCCTGTCTGTGACTCCAGGAGATAGCGTCAGTCTTTCCTG
CAGGGCCAGCCAAAGTATTAGCAACAACCTACACTGGTATCAACAAAAATCACATGAGTCTCCAAGGCTTCTCATCAA
GTATGCTTCCCAGTCCATCTCTGGGATCCCCTCCAGGTTCAGTGGCAGTGGATCAGGGACAGATTTCACTCTCAGTA
TCAACAGTGTGGAGACTGAAGATTTTGGAATGTATTTCTGTCAACAGAGTAACAGCTGGTGGACGTTCGGTGGAGGC
ACCAAGCTGGAAATCAAACGGGCTGATGCTGCACCAACTGTATCCGCATGCACC

Average
MFI B6: 95
MFI KO: 90
anti-CD3/CD28
MFI B6: 3360
MFI KO: 900
anti-CD3/CD28 + TGFβ1
MFI B6: 5737
MFI KO: 1000
anti-CD3/CD28 + IL-2
MFI B6: 3438
MFI KO: 927
anti-CD3/CD28 + TGFβ1 + IL-2
MFI B6: 5000
MFI KO:1200
BAMBI Not Stimulated
αCD3 + αCD28
54 kDa
27 kDa
21 kDa
BAMBI
N-Ras Arthritis
Clinical Severity
25
20
15
10
5
0
2
4
6
8
Days
Psoriasis
% of Thickening
100
80
60
40
20
0
2
4
6
Days
B10RIII
B10RIII.KO
B10RIII + B101.37

Colon Length (cm)
9
8
7
6
5
4
**
**
*

DAI
Days
0
1
2
3
4
5
6
7
8
● B6 ○ KO ▲ B6 + B101-37

MONOCLONAL ANTIBODIES AGAINST BAMBI AND USE FOR THE TREATMENT OF INFLAMMATORY DISEASES

CROSS-REFERENCE TO RELATED APPLICATIONS

The present patent application is a national phase application of International Application No. PCT/ES2016/070852, filed Nov. 30, 2016, which claims priority to Spanish Application No. P201531761, filed Dec. 3, 2015, the disclosures of which are incorporated herein by reference.

INCORPORATION BY REFERENCE

The content of the ASCII text file of the sequence listing named "SEQUENCE_LIST_EN_corrected", which is 4,873 b in size, was created on and electronically submitted via EFS-Web Jul. 16, 2019, is incorporated herein by reference in its entirety. This Sequence Listing consists of [SEQ ID NOs: 1-11].

The present invention relates to antibodies against the BAMBI (BMP and Activin Membrane Bound Inhibitor) protein and the use thereof for the treatment and prevention of inflammatory diseases. Therefore, the present invention falls within the field of medicine.

STATE OF THE ART

Under the name "autoimmune or chronic inflammatory" disease, there are currently more than 100 nosological entities that globally affect approximately 10% of the world's population (Shoenfeld Y et al. 2008 J Autoimmun 31:325). Autoimmune diseases are the result of the action of multiple environmental agents on a specific genetic and/or epigenetic background. The accumulation of all of these factors in an individual alters the regulation of the immune response, causing aberrant immune responses against external agents or the reaction of the system against itself. The consequence is the development of autoinflammatory and/or autoimmune diseases.

Among the autoimmune diseases, rheumatoid arthritis (RA), psoriasis, inflammatory bowel disease, spondyloarthritis and systemic lupus erythematosus are included, which share a series of etiopathogenic mechanisms, as well their response to similar or equal immunomodulatory or immunosuppressive treatments. RA is the most common autoimmune rheumatic disease.

Especially involved in autoimmune-based diseases are CD4+ T lymphocytes, a term that refers to multiple effector (TH1, TH2, TH17, TFH) or regulatory (Treg, Tr1) sub-populations, basically defined by the cytokine patterns they secrete (Zhu J et al. 2010 Annu Rev Immunol 28:445; Zygmunt B et al. 2011 Adv Immunol 109:159). Alterations in the control of mechanisms that regulate the differentiation and activation of the different functional CD4+ T lymphocytes sub-populations have been implied in the development of immune-based pathologies. In this sense, some severe autoimmune diseases have been associated with the uncontrolled increase in the differentiation and/or functionality of TH17 lymphocytes (Röhn T A et al. 2006 Eur J Immunol 36:2857; Kebir H et al. 2007 Nat Med 13:1173; multiple sclerosis or rheumatoid arthritis, among others) or TFH (Tangye S G et al. 2013 Nat Rev Immunol 13:412; systemic lupus erythematosus). On the other hand, the reduction in the number and/or suppressive activity of Tregs cells is critical in IPEX syndrome, seen in patients with foxp3 gene mutations (Bennett C L et al. 2001 Nat Genet 27:20) or in scurfin-deficient mice (Khattri R et al. 2003 Nat. Immunol 4:337).

For the treatment of autoimmune diseases, immunosuppressive drugs with a low degree of specificity have been used, and therefore they have multiple adverse side effects. More recently, cytokine-specific monoclonal antibodies or soluble receptors of said factors (globally known as biological drugs) have been used. These compounds have an advantage in that they have a high degree of specificity and the results obtained from them have been very positive. However, the use of biological drugs is not exempt from serious side effects, and furthermore, resistance appearance to the same is common, which forces the treatments to be stopped. Therefore, it is essential to develop highly specific therapies using monoclonal antibodies against new biological targets.

DESCRIPTION OF THE INVENTION

The present invention shows the use of monoclonal antibodies against BAMBI for the treatment and prevention of autoimmune diseases, the same being exemplified with recognized models of arthritis, psoriasis and colitis.

In a first aspect the present invention relates to a monoclonal antibody that specifically recognizes an amino acid sequence that comprises a peptide with at least an 80% identity with SEQ ID NO: 1, preferably an 80, 81, 82, 83, 84, 85, 86, 87, 88, 89, 90, 91, 92, 93, 94, 95, 96, 97, 98, 99 or 100% identity, wherein the length of said amino acid sequence is between 15 and 30 amino acids (15, 16, 17, 18, 19, 20, 21, 22, 23, 24 or 25 amino acids), preferably 25 amino acids.

The term "antibody", as used in the present invention, relates to immunoglobulin molecules and immunologically active portions (or fragments) of immunoglobulin molecules. That is, it refers to molecules that specifically bind (are immunoreactive) to an antigen, such as, for example, a peptide or a protein (an immunogen or epitope). The term "antibody" comprises monoclonal antibodies and polyclonal antibodies, and in the present invention the antibody is monoclonal, and it refers to an antibody that is intact or to immunologically active fragments of the same, and includes human, humanized and non-human, recombinant, chimeric and synthetic antibodies. In the context of this invention, the term antibody refers to the immunoglobulin that the animal or a hybrid cell has specifically synthesized against the sequence described in the first aspect of the present invention.

Examples of portions or fragments of immunologically active immunoglobulins include fragments F(ab) and F(ab')2, which can be generated by treating the antibody with an enzyme, such as pepsin.

"Monoclonal antibodies" are homogenous populations of identical antibodies, produced by a hybridoma, that is, a hybrid cell that is the product of the fusion of a clone of B lymphocytes descendant of a single and unique stem cell and a plasma cell tumor, which are directed against a specific site or antigenic determinant. The method for obtaining monoclonal antibodies of the invention can be carried out according to conventional methods known in the state of the art. Optionally, said antibodies can be purified by conventional means, such as affinity chromatography, protein A-Sepharose, hydroxyapatite chromatography, gel electrophoresis or dialysis.

As is known by a person skilled in the art, there are five isotypes or main classes of immunoglobulins: immunoglobulin M (IgM), immunoglobulin D (IgD), immunoglobulin G (IgG) (which in turn have the following subtypes in mice: IgG1, IgG2a, IgG2b and IgG3), immunoglobulin A (IgA) and immunoglobulin E (IgE). The monoclonal antibodies included in the present invention are: clone B101-37 (IgG1) and clone B143-14 (IgM).

In a preferred embodiment of the first aspect of the invention, the antibody specifically recognizes the sequence SEQ ID NO: 1: murine BAMBI(109-133) peptide:

```
LHDVLSPSKSEASGQGNRYQHDSSR
or

SEQ ID NO: 2: human BAMBI peptide (109-133):
LHDVLSPPRGEASGQGNRYQHDGSR.
```

A more preferred embodiment of the first aspect of the invention relates to the antibody wherein said antibody is expressed from the cell line (hybridoma) deposited in an international authority.

In a specific embodiment the antibody can comprise a detectable label. An even more preferred embodiment of the first aspect of the invention relates to the antibody wherein said antibody is conjugated with a fluorochrome, an enzyme, a gold particle, a nanoparticle, a peptide or another protein of interest, for example a protein or peptide ligand of a receptor.

The term "detectable label" or "tackle" in the present invention refers to a molecular tag that allows for the detection, location and/or identification of a molecule to which it is bound, by means of suitable detection methods and equipment, either by spectroscopic, photochemical, biochemical, immunochemical or chemical means. Examples of detectable labels for marking compounds include, but are not limited to, radioactive isotopes, enzymatic substrates, cofactors, ligands, chemiluminescent agents, fluorophores, enzymes (for example peroxidase), receptors and combinations thereof. In a specific embodiment the antibody is marked with biotin, avidin, streptavidin, alkaline phosphatase or horseradish peroxidase (HRP). Methods for marking and guiding the selection of suitable tackles for different purposes are known by a person skilled in the art.

The monoclonal antibody can be biochemically altered, by genetic manipulation or it can be synthetic; it may also lack portions.

In a more preferred embodiment of the first aspect of the invention, the antibody specifically comprises a heavy chain comprising the sequence SEQ ID NO: 3 and/or a light chain comprising the sequence SEQ ID NO: 4.

In another more preferred embodiment of the first aspect of the invention, the antibody comprises a heavy chain which comprises the sequence SEQ ID NO: 5 and/or a light chain which comprises the sequence SEQ ID NO: 6.

In a preferred embodiment, the antibody is the antibody in the present invention named clone B101-37 (IgG1, K anti-BAMBI) and/or clone B143-14 (IgM, κ anti-BAMBI).

In a specific embodiment, the present invention also relates to a gene construction that is able to generate the antibody of the first aspect of the present invention.

The term "identity", as used in this specification, refers to the proportion of identical amino acids between two compared peptides or proteins. The methods for comparing sequences are known in the state of the art, and include, but not limited to, the programs BLASTP or BLASTN, ClustalW and FASTA. We can consider that peptides or proteins with percent identities of at least 80% will maintain the same properties as the sequence SEQ ID NO: 1.

"Specific recognition", "specific binding" is understood as the binding (reaction, interaction or specific binding) between the antibody of the invention and the sequence described in the first aspect of the invention.

A second aspect of the present invention relates to an antiserum comprising the antibody of the first aspect of the invention.

The term "antiserum" relates to a serum obtained after the immunization of an animal with an immunogen. The antiserum comprises specific antibodies of said immunogen generated after the immune response produced in the animal. In the context of the present invention, the immunogen is the peptide with at least 80% identity with the sequence SEQ ID NO: 1 (preferably 80, 81, 82, 83, 84, 85, 86, 87, 88, 89, 90, 91, 92, 93, 94, 95, 96, 97, 98, 99 or 100%), preferably SEQ ID NO: 1 or SEQ ID NO: 2, and the antiserum comprises specific monoclonal antibodies generated against said sequence.

A third aspect of the present invention relates to a cell that expresses the antibody of the first aspect of the invention (hybridoma).

A fourth aspect of the present invention relates to the use of the antibody of the first aspect of the invention or of the antiserum of the second aspect of the invention for the inhibition of BMP and Activin Membrane Bound Inhibitor (BAMBI).

A fifth aspect of the present invention relates to the use of the antibody of the first aspect of the invention or of the antiserum of the second aspect of the invention for the manufacture of a medicament. Alternatively, the present invention further relates to the antibody of the first aspect of the invention or of the antiserum of the second aspect of the invention, for use as a medicament.

A sixth aspect of the present invention relates to the use of the antibody of the first aspect of the invention or of the antiserum of the second aspect of the invention for the manufacture of a medicament for the treatment or prevention of autoimmune diseases. Alternatively, the present invention also relates to the antibody of the first aspect of the invention or of the antiserum of the second aspect of the invention for use as a medicament for the treatment or prevention of autoimmune diseases.

In the present invention the term "autoimmune disease" is understood as a disease in which the cells of the immune system trigger a chronic inflammatory response in one or several tissues of the individual, causing the deterioration or even destruction thereof. In the present invention, the terms "autoimmune disease" and "chronic inflammatory disease" are used interchangeably.

The autoimmune disease is preferably autoimmune arthritis, inflammatory bowel disease, psoriasis, spondyloarthritis or systemic lupus erythematosus. In an even more preferred embodiment the autoimmune arthritis is recent-onset arthritis or rheumatoid arthritis.

For this reason, in a more preferred embodiment of the sixth aspect of the invention, the autoimmune diseases are chosen from the list consisting of: autoimmune arthritis, spondyloarthritis, psoriasis, systemic lupus erythematosus, and inflammatory bowel disease. Preferably, the inflammatory bowel disease is ulcerative colitis or Crohn's disease.

In the present invention the term "autoimmune arthritis" include both the terms "Rheumatoid Arthritis" and "Undifferentiated Arthritis", regardless of whether it is recent-onset or well-established arthritis.

In the present invention, "Recent-Onset Arthritis Disability" (ROAD) (or early arthritis) is a disease consisting of inflammation of at least one joint, in less than one year of development, which complies with the pre-established criteria by the American College of Rheumatology (ACR) and EULAR of "Rheumatoid Arthritis or RA" (Aletaha, Neogi et al. Ann Rheum Dis 2010; 69:1580-1588) or, without complying with said criteria, does not comply with criteria of other autoimmune, degenerative or metabolic diseases that may explain the symptoms. This last case is termed "Undifferentiated Arthritis" (UA) which, in many cases, if left untreated, ends up becoming RA. In this invention the terms ROAD, RA or UA refer to a chronic and progressive systemic autoimmune disease which causes chronic inflammation, primarily in the joints, and which, given the progressive nature thereof, causes the destruction thereof, resulting in deformation and loss of functional ability thereof. Furthermore, this disease can cause extra-articular alterations in different organs.

In the present invention the term "spondyloarthritis" is understood as any autoimmune disease, axial and/or peripheral, which meets the classification criteria of the *Assessment of SpondyloArthritis International Society* (ASAS) (Rudwaleit et al. Ann Rheum Dis 2011; 70:25-31).

In the present invention, "systemic lupus erythematosus" is understood as any systemic autoimmune disease defined by the criteria of the American College of Rheumatology (Tan et al. Arthritis Rheum• 1982; 25:1271-1277).

In the present invention, the term "inflammatory bowel disease" or "IBD" refers to chronic inflammation of the intestine in an individual, wherein said inflammation is due to the very immune system of the individual. The two most common forms are ulcerative colitis and Crohn's disease. Therefore, in a preferred embodiment, the autoimmune disease is ulcerative colitis or Crohn's disease.

In the present invention, "psoriasis" is understood as any skin disease that is characterized by an improper functioning of the immune system which causes an excessive production of skin cells. This disease causes the formation of red bumps covered by dry scales. Furthermore, excessive cell production also causes the infiltration of white blood cells on the skin. Generally, injuries are located in areas with the greatest friction, such as, although not limited to, the elbows, knees or groin area.

A seventh aspect of the present invention relates to a pharmaceutical composition comprising the monoclonal antibody of the first aspect of the invention or of the antiserum of the second aspect of the invention.

In this specification, the term "pharmaceutical composition" refers to any substance used for the diagnosis, prevention, alleviation, treatment or cure of a disease in a human being or in animals. The pharmaceutical composition of the invention can be used alone or in combination with other pharmaceutical compositions. In a preferred embodiment, the pharmaceutical composition further comprises a pharmaceutically acceptable carrier or excipient.

The term "excipient" refers to a substance which helps the absorption of the pharmaceutical composition, comprising the antibody of the invention, stabilizes said pharmaceutical composition or helps in the manufacture thereof in the sense of giving it consistency, form, flavor or any other specific functional characteristic. Thus, excipients could have the function of keeping the ingredients bound together, such as for example starches, sugars or celluloses, a sweetening function, a colorant function, a protection function, such as for example isolating it from the air and/or moisture, a filler function for a tablet, capsule or any other form of formulation, such as for example dibasic calcium phosphate, a disintegrating function to facilitate the dissolution of the components and their absorption, without excluding other types of excipients not mentioned in this paragraph.

A "pharmaceutically acceptable carrier" (or "pharmacologically acceptable") refers to any substance, or combination of substances, known in the pharmaceutical sector, used in the manufacture of pharmaceutical forms of administration and includes, but is not limited to, solids, liquids, solvents or surfactants. The carrier can be an inert substance or have a similar action to any of the compounds of the present invention, having the function of facilitating the incorporation of the drug as well as other compounds, allowing for an improved dosage and administration or providing consistency and form to the pharmaceutical composition. When the dosage form is liquid, the carrier is the diluent. The term "pharmacologically acceptable" refers to the fact that the compound referred to is allowed and evaluated so that it does not cause harm to the organisms to which it is administered.

The pharmaceutical composition of this invention can be facilitated through any route of administration, and as such, said composition shall be formulated in the pharmaceutical form suitable to the chosen route of administration.

An eighth aspect of the present invention relates to the in vitro use of the antibody of the first aspect of the invention or of the antiserum of the second aspect of the invention for the screening of drugs, preferably drugs for the treatment or prevention of autoimmune diseases. The autoimmune diseases are preferably chosen from a list that consists of: autoimmune arthritis, spondyloarthritis, psoriasis, systemic lupus erythematosus, and inflammatory bowel disease. More preferably the inflammatory bowel disease is ulcerative colitis or Crohn's disease.

The term "in vitro" relates to the fact that the method of the invention is done outside of the body of the subject. That is, it is done on a biological sample of a subject.

In the present invention, the term "biological sample" refers to any sample that allows for the screening of drugs, and includes, but is not limited to, biological fluids or tissues of an individual, obtained by means of any method known by a person skilled in the art that serves for said end. For example, the biological sample could be, but is not limited to, a fluid sample, such as blood, plasma, serum or tissue. The biological sample of the present invention can be fresh, frozen, fixed or fixed and paraffin embedded.

In the present invention the terms "subject" and "individual" are used interchangeably. As used in the present document, the term "subject" or "individual" refers to all animals classified as mammals and includes, but is not limited to, farm and domestic animals, primates and humans, for example human beings, non-human primates, cows, horses, pigs, sheep, goats, dogs, cats or rodents. Preferably, the subject is a human being, male or female, of any age or race.

A ninth aspect of the present invention relates to a method for obtaining a monoclonal antibody that recognizes an amino acid sequence comprising a peptide with at least an 80% identity with the sequence SEQ ID NO: 1, comprising:

a. obtaining previously extracted serum from a non-human animal immunized with a recombinant protein comprising an amino acid sequence comprising a peptide with at least an 80% identity with the sequence SEQ ID NO: 1;
b. obtaining a hybridoma from step a) which generates specific monoclonal antibodies against an amino acid sequence comprising a sequence with at least an 80% identity with SEQ ID NO: 1.

In a more preferred embodiment of the ninth aspect of the invention, the method further comprises a step (c) of isolating the monoclonal antibody from the hybridoma generated in step (b).

In another more preferred embodiment of the ninth aspect of the invention, in step (a) the amino acid sequence is the sequence SEQ ID NO: 1 or SEQ ID NO: 2.

In an even more preferred embodiment of the sixth aspect of the invention, the non-human animal is a mammal that is chosen from a list consisting of pigs, chimpanzees, mice, rats, rabbits and guinea pigs.

A tenth aspect of the present invention relates to a kit and/or device, herein after shall be referred to "kit of the invention" or "device of the invention", comprising the antibody, the antiserum, the cell, as described in the invention, and/or any combination thereof.

The kit and/or device of the invention can further comprise, but is not limited to, probes, buffers, enzymes, agents for preventing contamination, etc. On the other hand, the kit can include all of the necessary supports and containers for the start-up and optimization thereof. The kit can further contain other proteins, including antibodies or antigens, which serve as positive and negative controls. Preferably, this kit further comprises the instructions for detecting the BAMBI protein, preferably by means of an immunohistochemical assay, more preferably by means of ELISA, Western blot or immunofluorescence.

Optionally, the antibody of the invention in the kit is marked or immobilized.

The term "marked", as used in the present description, refers to the fact that the antibody is conjugated with a label. A high number of labels that can be conjugated to an antibody are known in the state of the art. Examples of labels that can be used for marking an antibody are, without limitation, radioisotopes (for example, 32P, 35S or 3H) fluorescent or luminescent markers [for example, fluorescein isothiocyanate (FITC), rhodamine, texas red, phycoerythrin (PE), allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4,7',4,7-hexachlorofluorescein (HEX), 5-carboxyfluorescein (5-FAM) or N,N,N',N'-tetramethyl-6-carboxyrhodamine (TAMRA)]; antibodies, fragments F(ab)2)], affinity labels [for example, biotin, avidin, agarose, bone morphogenetic protein (BMP) haptens], enzymes or enzyme substrates [for example, alkaline phosphatase (AP) and spicy horseradish peroxidase (HRP)].

The term "immobilized", as used in the present description, refers to the fact that the antibody of the invention can be bound to a support without losing its activity. Preferably, the support can be the surface of an array (for example, a nylon array), a microtiter plate (for example, with 96 wells) or a similar plastic support, or beads (spheres, for example, agarose spheres or small superparamagnetic microspheres made up of biodegradable arrays).

Another aspect of the invention relates to the in vitro use of the kit of the invention for detecting a peptide with at least an 80% identity with SEQ ID NO: 1. In a more preferred embodiment, the kit is used for detecting the peptide of SEQ ID NO: 1 or SEQ ID NO: 2.

In another aspect, the present invention relates to the in vitro use of the kit and/or device of the invention for the treatment and/or prevention of autoimmune diseases. In a more specific embodiment of this aspect, the autoimmune diseases are chosen from a list that consists of: autoimmune arthritis, spondyloarthritis, psoriasis, systemic lupus erythematosus, and inflammatory bowel disease, more specifically the inflammatory bowel disease is ulcerative colitis or Crohn's disease.

Another object of the invention is constituted by a method for treating and/or preventing autoimmune diseases which comprises administering a therapeutically effective amount of the antibody of the invention, of the antiserum of the invention, or of the composition of the invention to a subject in need thereof.

For the purposes of the present invention, the term "treatment" refers to an intervention performed with the intention of preventing the development or altering the pathology of a disorder. Thus, "treatment" refers both to therapeutic treatment as well as to prophylactic or preventative measures. A "subject in need of treatment" includes any case in which said subject already has the disorder, as well as any case in which the disorder is to be prevented. In the treatment of an immunological type disease, a therapeutic agent can directly alter the magnitude of the response of an immune response component, or make the disease more susceptible to treatment by other therapeutic agents, such as antibiotics, antifungals, anti-inflammatory agents, chemotherapeutic agents, etc. Administration can take place "in combination with" one or more therapeutic agents and includes simultaneous (concurrent) and consecutive administration in any order.

For the purposes of the present invention, the term "therapeutically effective amount" refers to the amount of antibody, antiserum or composition of the invention required to achieve an appreciable improvement in the state, for example, a pathology, of the disease or condition which is the object of the treatment.

In a preferred embodiment of the method of treatment and/or prevention of the invention, the same is characterized in that the autoimmune diseases are chosen from a list that consists of: autoimmune arthritis, spondyloarthritis, psoriasis, systemic lupus erythematosus and inflammatory bowel disease, and more specifically the inflammatory bowel disease is ulcerative colitis or Crohn's disease.

Throughout the description and the claims, the word "comprises" and its variants are not intended to exclude other technical characteristics, additives, components or steps. For those skilled in the art, other objects, advantages and characteristics of the invention may be deduced from both the description and the practical use of the invention. The following examples and drawings are provided by way of illustration, and are not meant to limit the present invention.

BRIEF DESCRIPTION OF THE FIGURES

FIGS. 1A-1C illustrate characterization of the murine anti-BAMBI(109-133) mAbs B101-37 and B143-14. FIG. 1A illustrates specificity of the anti-BAMBI mAbs B101-37 and B143-14 evaluated by Western Blot in heart cell membrane lysates from normal B6 and B6.BAMBI-KO mice. FIG. 1B illustrates recognition of human BAMBI by the mAb B101-37 evaluated by Western Blot in human heart cell membrane lysates. FIG. 1C illustrates CDR sequence of heavy and light chains of the mAbs B101-37 and B143-14. The VDJ and VJ recombination of the heavy and light chains, respectively, of both mAbs are indicated.

FIG. 2A illustrates comparative analysis by means of flow cytometry of the expression of BAMBI in CD4+ T lymphocytes of normal B6 and B6.BAMBI-KO mice before, and 48 hours after in vitro activation thereof with anti-CD3 and anti-CD28 antibodies in the presence or absence of TGFβ or IL-2 (top panels). On the bottom panels, the staining with B101-37 of the CD4+ T lymphocytes activated in B6.BAMBI-KO mice is compared with that of the IgG1 isotype control in CD4+ T lymphocytes activated in normal mice. FIG. 2B illustrates induction of BAMBI in human T lymphocytes stimulated in vitro for 48 hours with anti-CD3 and anti-CD28 mAbs. The BAMBI expression was analyzed by Western Blot in plasma membrane lysates. As loading control, the N-Ras expression was compared in the same lysates.

FIG. 3A illustrates naive CD4+CD25-CD62L+CD44− T cells of normal B6 and BAMBI-KO mice were stimulated for 5 days with anti-CD3 and anti-CD28 antibodies in Treg (top panels) or TH17 (bottom panels) polarizing conditions in the presence of mAb B143-14 (IgM anti-BAMBI) or a mouse polyclonal IgM (Sigma). FIG. 3B illustrates human naive CD4+ T lymphocytes purified by magnetic separation were activated in vitro for 10 days with anti-CD3 and anti-CD28 antibodies conjugated to beads in TH0 or Treg differentiation conditions and in the presence of mBa B143-14 (IgM anti-BAMBI) or a mouse polyclonal IgM. The percentages of CD4+FoxP3+ cells are shown, analyzed by means of flow cytometry in TH0 differentiation conditions (white bars) and Treg differentiation conditions (black bars). FIG. 3C illustrates human CD4+ T lymphocytes, purified by magnetic separation, were activated in vitro for 10 days with anti-CD3 and anti-CD28 antibodies conjugated to beads in TH0 or TH17 differentiation conditions. The inhibition effect of BAMBI with the mAb B143-14 on the differentiation into TH17 cells, either IFNg producers or not, analyzed by means of flow cytometry, is shown. The statistical differences are represented as: **p<0.01.

FIG. 4A and FIG. 4B illustrate CIA induction, normal B10RIII mice were immunized with bovine type II collagen emulsified in CFA. The different experimental groups received treatments with 2 mg/mouse/week, 0.3 mg/mouse/week of B101-37 or with 2 mg/mouse/week of irrelevant murine IgG1 (IgG1-C) during the first 4 weeks after immunization. The clinical degree of severity of each mouse (FIG. 4A) and of different radiological injuries (average±SD) associated with articular destruction at the eighth week after immunization is shown (FIG. 4B). As controls for the aforementioned experiments, the development of CIA between normal B10RIII and BAMBI-KO mice was compared. The evolution of the clinical severity of arthritis in these animals, expressed as average±SD. (FIG. 4C) and of different radiological injuries (average±SD) associated with the articular destruction at the eighth week after immunization is shown (FIG. 4D). The statistical differences are represented as: *p<0.05, **p<0.01.

FIG. 5A illustrates normal B10RIII or BAMBI-KO mice treated or not treated from the beginning of the experiment with mAb B101-37 (2 mg/mouse/week) received an IP injection of 10 mg of mannan obtained from the yeast *Saccharomyces cerevisiae*. The evolution of the severity of the arthritis and of the percentage of the increase in ear thickness (average±SD) in the different experimental groups is shown. FIG. 5B illustrates photographs showing the macroscopic appearance of the auricle of the experimental groups described in (A). The statistical differences are represented as: *p<0.05, p<0.01, * p<0.001.

FIG. 7A illustrates evolution of the clinical severity of the cutaneous injuries, evaluating the appearance and severity of erythema, desquamation of the skin and thickness of the ear treated in comparison with the non-treated contralateral ear. FIG. 7B illustrates histologic severity of the cutaneous injuries. The top photographs show representative examples (×10) of histologic cuts of the ears stained with haematoxylin and eosin. The lower panels show the values of the thickness of the epidermis (left panel) and of the dermis (right panel) in the different animals of each experimental group. The statistical differences are represented as: *p<0.05, *** p<0.001.

FIG. 8C illustrates mortality in the different experimental groups. The statistical differences are represented as: *p<0.05, **p<0.01.

EXAMPLES

Figure 1A:
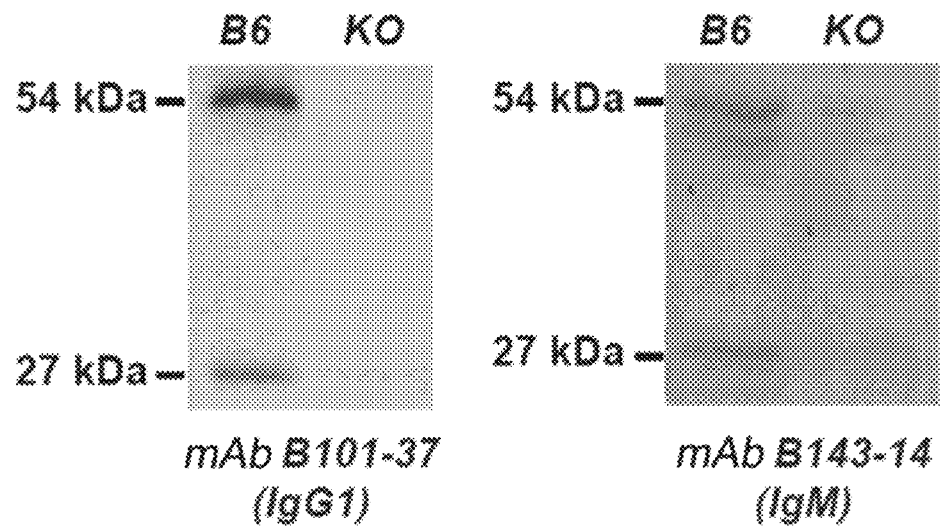

The invention is illustrated below by means of tests carried out by the inventors which reveal the effectiveness of the product of the invention.

Material and Methods.

Obtention and Characterization of the Murine Anti-BAMBI Monoclonal Antibodies.

B6.BAMBI-KO mice were immunized with the murine BAMBI(109-133) peptide conjugated to keyhole limpet hemocyanin (KLH) and emulsified in complete Freund's adjuvant (CFA). The mice were immunized on two more occasions (with one month difference between each immunization) with the same peptide emulsified in incomplete Freund's adjuvant (IFA). The murine BAMBI(109-133) peptide is located in the extracellular region of BAMBI and differs from its human homologue by 4 amino acids (positions 8, 9, 10 and 23 of the SEQ ID NO: 1). The presence of murine anti-BAMBI(109-133) circulating antibodies in immunized mice was evaluated 15 days after each immunization by means of ELISA. Mice with higher titers of these antibodies were used for obtaining the murine anti-BAMBI monoclonal antibodies (mAb). To do so, spleen cell suspensions were fused with non-secreting myeloma cell line SP2/O—Ag14 as was previously described (Yokoyama W M. et al. Curr Protoc Immunol. 2013, Unit 2.5). Hybridoma that produce human anti-BAMBI mAb were selected by enzyme-linked immunosorbent assay (ELISA). In the present invention, two of the mAbs obtained have been characterized; clone B101-37 (igG1, k anti-BAMBI) and clone B143-14 (IgM, k anti-BAMBI). The specificity of the mAbs was subsequently evaluated by means of Western Blot in heart cell membrane of hearts from normal B6 and B6.BAMBI-KO mice and of human myocardial samples obtained from surgical biopsies.

Ribonucleic acid (RNA) of mAbs B101-37 and B143-14 were isolated by means of the commercial kit RNeasy Mini Kit (Qiagen). For defining the encoding sequences for the complementarity-determining regions of (CDRs) in the heavy and light chain of both mAbs, RT-PCRs were carried out based on the purified RNAs, as previously described (Wang Z. et al. J Immunol Methods. 2000, 233:167). For defining the CDR of the heavy chain of B101-37, the following amplicons were used: degenerate amplicon 5' from the FR1 region of the heavy chain: 5'-CTT CCG GAA TTC SAR GTN MAG CTG SAG SAG TC-3 (SEQ ID NO: 7)'; amplicon 3' of the constant region of IgG1: 5'-GGA AGA TCT ATA GAC AGA TGG GGG TGT CGT TTT GGC-3' (SEQ ID NO: 8). For defining the CDR of the heavy chain of B143-14, the previously mentioned degenerate amplicon from the FR1 region of the heavy chain and the amplicon 3' of the constant region of IgM were used: 5'-GGA AGA TCT GAC ATT TGG GAA GGA CTG ACT CTC-3' (SEQ ID NO: 9). For defining the CDR of the heavy chain of B101-37 and B143-14, the following amplicons were used: degenerate amplicon from the FR1 region of the light chain k: 5'-GG GAG CTC GAT ATT GTG MTS ACM CAR WCT MCA-3' (SEQ ID NO: 10); amplicon 3' of the constant region of the light chain k. 5'-GGT GCA TGC GGA TAC AGT TGG TGC AGC ATC-3' (SEQ ID NO: 11). The PCR products were subsequently sequenced (STABVida, Caparica, Portugal) and the sequences were analyzed by means of the IgBLAST program.

Study of BAMBI Expression in Murine and Human CD4 T Lymphocytes.

By means of flow cytometry BAMBI expression in CD4+ T lymphocytes of normal B6 mice after the stimulation thereof using biotinylated mAb B101-37. The isolated CD4+ T lymphocytes of the spleen of normal B6 mice were stimulated in vitro for 48 hours with antibodies anti-CD3 (1 μg/well) and anti-CD28 (0.5 μg/well) bound to the plate in the presence or absence of 2 ng/ml of recombinant murine TGFβ and/or 1 ng/ml of recombinant murine IL-2 (PeproTech, London). As negative controls, spleen cells of B6.BAMBI-KO mice stimulated in the same way and colored with biotinylated B101-37 and normal B6 mice colored with a biotinylated isotype control were used. The colored cells were analyzed in a FACSCanto II cytometer equipped with FACSDiva software (BD Biosciences).

BAMBI expression in human CD4+ T lymphocytes after the in vitro stimulation thereof was analyzed by means of Western Blot. Said lymphocytes were purified from 50 ml of buffy coats coming from healthy donors of the Blood and Tissues Bank of Cantabria (Marques de Valdecilla University Hospital, Santander). The mononuclear cells obtained after the Ficoll gradient were subjected to a positive selection after marking with specific mAb of CD4 conjugated to magnetic microparticles (MACS) using a magnetic separator (AutoMACS, Miltenyi Biotec). The CD4+ T lymphocytes were subsequently stimulated in vitro for 48 hours with antibodies anti-CD3 (1 μg/well) and anti-CD28 (0.5 μg/well) bound to the culture plate. The cell membrane lysates of the activated lymphocytes were obtained as described above.

In Vitro Differentiation Cultures of Murine and Human CD4+ T Lymphocytes into Treg and TH17 Cells.

The inhibiting capability of anti-BAMBI mAbs directed against the BAMBI(109-133) peptide were explored in vitro in murine and human CD4+ T lymphocyte cultures differentiated into Treg and TH17 cells. In these experiments, mAb B143-14 was used. In the experiments with murine lymphocytes, naïve CD4+ cells (CD4+CD25−CD62L+CD44−) from spleens of normal B6 mice were purified by means of cell sorting (FACSAria, BD Biosciences). $5\times10^5$ naïve CD4+ cells were stimulated for 5 days with anti-CD3 and anti-CD28 antibodies bound to the plastic of the culture plate, in Treg polarizing conditions (2 ng/ml of murine TGFβ) or TH17 (1 ng/ml of murine TGFβ and 10 ng/ml of murine IL-6) in the presence of 20 μg/ml of B143-14 or 20 μg/ml of murine IgM (Sigma, St Louis, Mo.) as an isotype control. The percentages of lymphocytes TCD4+FoxP3+ (Treg) and CD4+IL-17+(TH17) at the end of the culture were analyzed by means of flow cytometry, as was previously described (Iglesias M. et al. Arthritis Rheum 2013, 65:343).

Human naïve CD4+ T lymphocytes (in Treg differentiation) or CD45RO+ memory T lymphocytes (in TH17 differentiation), purified by magnetic separation, were activated in vitro for 10 days with anti-CD3 and anti CD28 antibodies (aBs) conjugated to beads in Treg differentiation conditions (5 ng/ml of TGFβ) or TH17 (20 ng/ml of IL-1β, 30 ng/ml of IL-6, 30 ng/ml of IL-23, 3 ng/ml of TGFβ1, 1 μg/ml of anti-IFNγ and 2.5 μg/ml of anti-IL-4) in the presence of 20 μg/ml of B143-14 or 20 μg/ml of murine IgM. The percentages of lymphocytes TCD4+FoxP3+(Treg) and CD4+IL−17+(TH17) at the end of the culture were analyzed by means of flow cytometry.

Experimental Model of Arthritis after Immunization with Bovine Type II Collagen Emulsified in CFA (CIA).

Groups of 10 B10RIII (MHC H-2r) BAMBI-deficient or not mice were immunized before their $12^{th}$ week of age by intradermal route at the root of the tail with 150 μg of bovine type II collagen (MD Biosciences, Zurich) emulsified (vol. 1/1) in CFA containing a concentration of *Mycobacterium tuberculosis* of 4 mg/ml (MD Biosciences) as was previously described (Iglesias M. et al. Arthritis Rheum 2013, 65:343). To study the effect of BAMBI inhibition in the development of CIA, normal B10RIII mice were intraperitoneally (IP) treated during the first 4 weeks after immunization with 2 or 0.3 mg/week of B101-37 or with 2 mg/week of anti-TNP IgG1 used as an isotype control (IgG1-C). The evolution of arthritis was monitored on a weekly basis from the 3rd week (the date on which arthritis began) to the eighth week after immunization. The severity of the arthritis was evaluated in each of the four extremities by means of the method described by Wooley et al (Wooley P H. et al. J Immunol 1985, 135:2443). Likewise, on the eighth week of immunization the articular injuries on the front and back legs were evaluated by means of radiology, as we previously described (Iglesias M. et al. Arthritis Rheum 2013, 65:343).

Experimental Model of Dextran Sulfate Sodium Colitis (DSS-Colitis).

For the induction of colitis, DSS (MPbio.com), DSS was dissolved in water at 3%. This solution (with daily changes of water) was administered in a bottle to the mice of the different experimental groups for a variable time period [until the mice of the control group reached an activity ratio of the disease (DAI) of between 1.5-2 (approximately 4-5 days)]. The water consumed by each experimental group was measured daily and the DAI was evaluated calculating the clinical score of the following parameters: A) weight loss: 0=no weight loss, 1=weight loss of 1.5%, 2=: weight loss of 5-10%, 3=weight loss of 10-20%, and 4=weight loss of more than 20%; B) fecal consistency (the same value is given to all animals that are in the same box). 0=normal fecal consistency, 2=soft feces and 4=diarrhea; C) rectal bleeding (the same value is given to all animals that are in the same box): 0=no blood, 2=minor bleeding and 4=intense bleeding. The final DAI value was calculated by adding the values of the different parameters and dividing by 3.

Mannan Induced Psoriatic Arthritis.

For the induction of acute symptoms of psoriatic arthritis, groups of B10RIII BAMBI-deficient mice, or mice not BAMBI-deficient received an IP injection of 10 mg of mannan obtained from *S. cerevisiae* yeast (Sigma-Aldrich) dissolved in 200 µl of PBS (Khmaladze I. et al. Proc Natl Acad Sci USA 2014, 111:E3669). Additionally, a chronic form of the process was induced in non-transgenic B10RIII mice by means of repeated injections of the same mannan dose once a week. To study the effect of the treatment with B101-37 on the prevention of psoriatic arthritis, mice that received a single mannan injection were treated from the moment of the administration of mannan (induction of the disease) with 2 mg/week of B101-37 or with 2 mg/week of an anti-TNP IgG1 used as IgG1-C. To evaluate the therapeutic effect of the treatment with B101-37, the non-transgenic B10RIII mice with the chronic form of the disease were treated with 2 mg/week of B101-37 (divided into 3 equal doses every two days) from the moment of the first mannan injection with (preventative treatment) or from the moment the first clinical signs of the process were observed (3 days after the first manna injection; therapeutic treatment) until the end of the experiment. Once again, as controls, non-transgenic B10RIII mice treated with an anti-TNP IgG1 from the moment of the appearance of the first signs of the disease were analyzed. The psoriatic injuries were evaluated at the level of the auricles, quantifying the thickness of the same with the help of a digital gauge. The severity of the arthritis was evaluated in each of the four legs, on a scale of 0-10 (total range of 0-40) in the following way: severe inflammation of the carpus/tarsus=5 points, adding an additional point for each inflamed toe. If the inflammation is minor=3 points per carpus/tarsus+0.5 points for each inflamed toe.

Experimental Model of Imiquimod Induced Cutaneous Psoriasis.

For the induction of cutaneous psoriasis, 12.5 mg of imiquimod (Aldara®) was topically applied for 6 days on the right ears of B10RIII mice, BAMBI deficient or not. The different experimental groups were treated at the moment of the first application of imiquimod with a single dose of 2 mg of B101-37 or of irrelevant murine IgG1. Erythema, desquamation and the increase in the thickness of the ear were evaluated daily. Erythema and desquamation were evaluated using a clinical score of 0 to 4 in the following way: none=0, minor=1, moderate=2, severe=3, highly severe=4. The increase in the thickness of the treated ear was calculated with the help of a digital gauge in comparison with the thickness of the non-treated left ear in the following way: no increase=0, increase of 0.1-10%, increase of 10.1-20%=2, increase of 20.1-30%=3, increase of 30.1-40%=4, increase of 40.1-50%=5. The animals were sacrifices 24 hours after the last application of imiquimod and skin samples were collected for the histological study. The thickness of the epidermis and the dermis in the histological samples from the ears treated with imiquimod were quantified in each animal using the ImageJ program, in relation to the respective thicknesses of the histological samples from the contralateral ears that were not treated.

Example 1: Molecular Characterization of Anti-BAMBI mAb

The specificity of the anti-BAMBI B101-37 and B143-14 mAbs was initially determined by means of ELISA (during the hybridoma screening process) and subsequently by means of Western Blot. Both mAbs recognize a band of approximately 27-29 kDa and another of approximately 54 kDa, compatible with BAMBI monomers and dimers resistant to sodium dodecyl sulfate (SDS) and reducing conditions, as was previously described (Xavier S et al. 2010 PLoS One 5:e12995) in lysates of B6 mice but not in those of B6.BAMBI-KO mice (FIG. 1A).

Figure 1B:
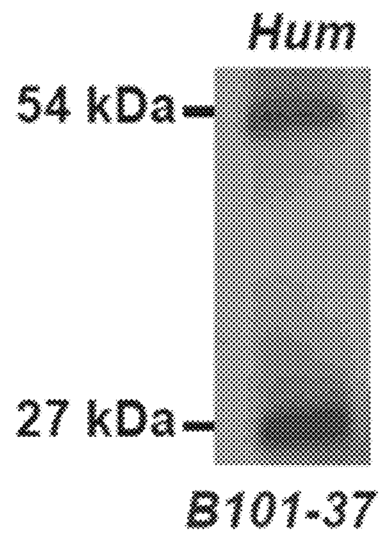

Although the murine BAMBI(109-133) peptide used for the development of anti-BAMBI mAb differs from its human homologue in 4 amino acids studied by Western Blot in myocardial plasma membrane lysates indicate that B101-37 also recognizes human BAMBI (FIG. 1B).

We subsequently characterize the CDRs of the heavy and light chains of both anti-BAMBI mAbs by means of deoxyribonucleic acid (DNA) sequencing (SEQ ID NO: 3, SEQ ID NO: 4, SEQ ID NO: 5, SEQ ID NO; 6). The comparison of the DNA sequences with the IgBLAST database indicates that the CDR of the heavy and light chains of mAb B101-37 are the result of the reordering of the V9-3/D1-3/J1 and V15-103/J5 segments, respectively, while the CDRs of the heavy and light chains of mAb B143-14 are the result of the reordering of the V1-55/D4-1/J2 and V5-43/J1 segments, respectively (FIG. 1C).

Example 2: BAMBI Expression in CD4+ T Lymphocytes

Figure 2A:
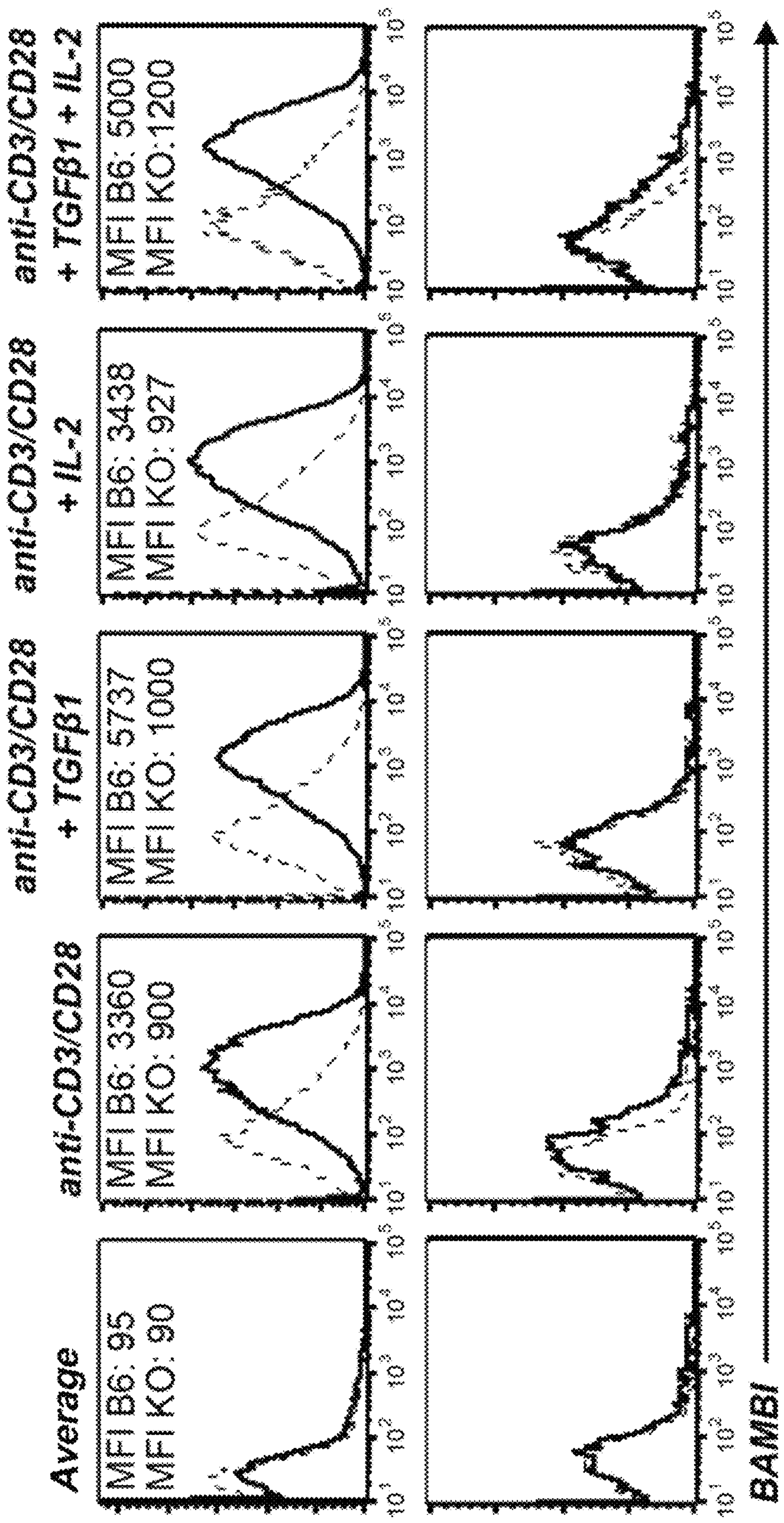
FIGS. 2A-2B illustrate the induction of BAMBI expression in murine and human CD4+ T lymphocytes after the activation thereof.

CD4+ T lymphocytes play a fundamental role in the development of inflammatory and autoimmune pathologies. For this reason, the regulation of BAMBI expression in this lymphocytic population in mice is studied by means of flow cytometry and subsequently in humans by means of Western Blot, in both cases using mAb B101-37. In murine naïve CD4+ T lymphocytes BAMBI expression was not detected, but it was induced 48 hours after the in vitro stimulation thereof with anti-CD3 and anti-CD28 antibodies (FIG. 2A). This expression increased after the addition of TGFβ, but not of IL-2, to the activated CD4+ T cells (FIG. 2A). As specificity controls of mAb B101-37, markers in flow cytometry were not detected in activated CD4+ T lymphocytes of BAMBI-KO mice colored B101-37 or in normal B6 mice colored with an isotype control IgG1, respectively (FIG. 2A, bottom panels).

Figure 2B:
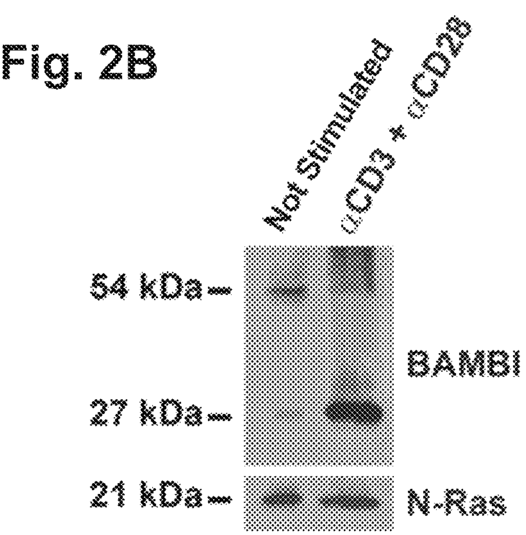

Just like in the mouse, BAMBI expression was very low in human naïve CD4+ lymphocytes, being induced after the stimulation thereof with anti-CD3 and anti-CD28 antibodies (FIG. 2B).

Example 3: BAMBI Inhibition with Murine Anti-BAMBI(109-133) mAb B143-14 Alters In Vitro Differentiation of the CD4+ T Lymphocytes of Mice and Humans into Subtypes Treg and TH17

Figure 3A:
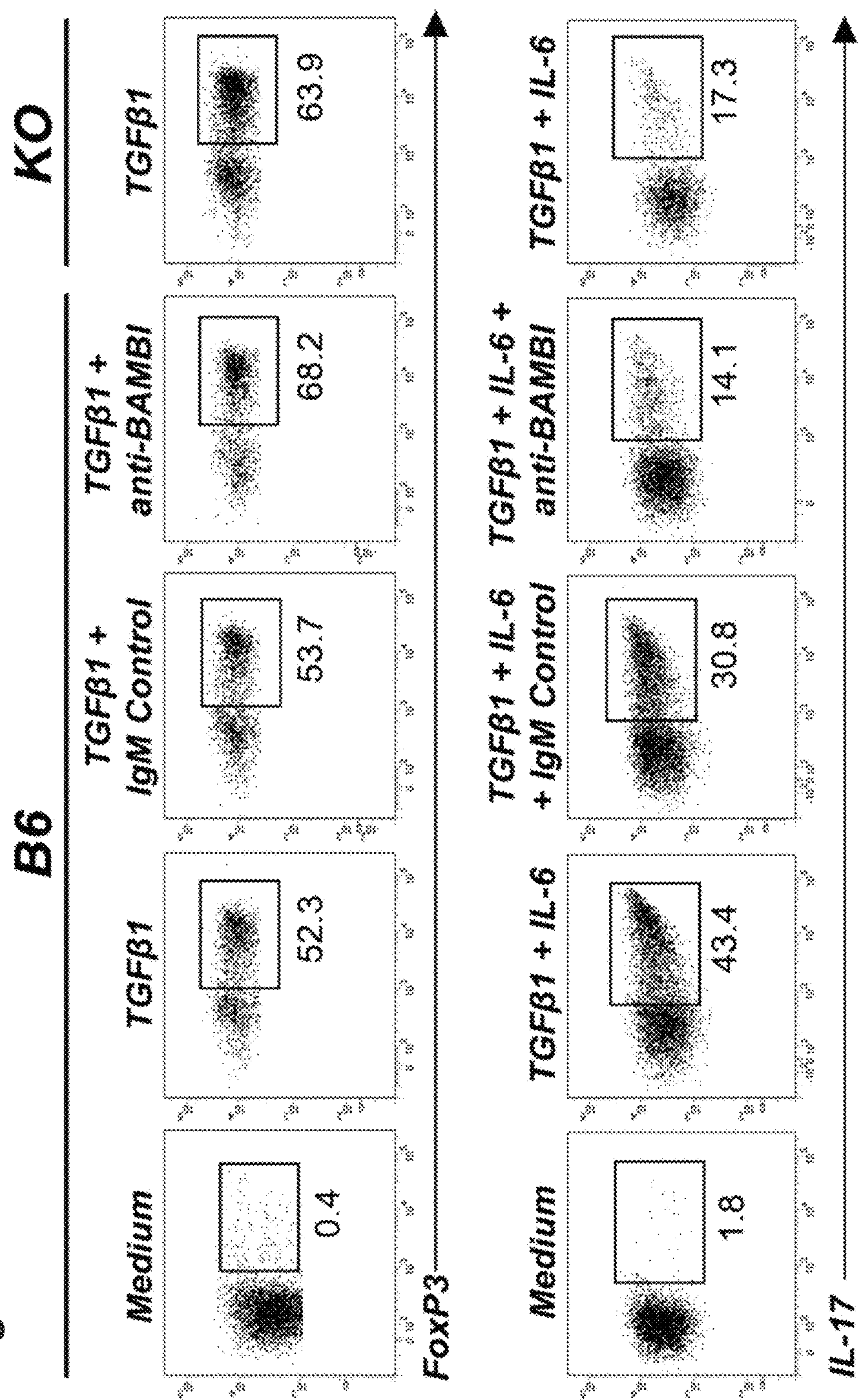
FIGS. 3A-3C illustrates the effect of the BAMBI inhibition on the in vitro differentiation of murine and human CD4+ T lymphocytes into Treg and TH17 cells.

In previous studies we showed that the absence of BAMBI in CD4+ T lymphocytes of BAMBI-KO mice strengthened and inhibited the in vitro differentiation thereof into Treg and TH17 populations, respectively (Postigo J et al. Doctoral Thesis defended on 19 Apr. 2013, University of Cantabria). To evaluate the inhibiting effect of the anti-BAMBI mAbs directed against the murine BAMBI(109-133) epitope, we analyzed the capability of B143-14 to alter the functional differentiation of the CD4+ T lymphocytes of normal mice in the same sense as that observed in BAMBI-KO mice. To do so, naïve CD4+ T lymphocytes of normal B6 and BAMBI-KO mice were activated in vitro in polarization conditions to Treg or TH17 cells, in the presence of B143-14 mAb or a murine IgM used as an isotype control. Just as observed with the lymphocytes of BAMBI-KO mice, the BAMBI inhibition after the addition to the B143-14 culture, but not of the IgM control, increased and reduced the Treg and TH17 in vitro differentiation, respectively, of CD4+ T lymphocytes of normal B6 mice (FIG. 3A).

Figure 3B:
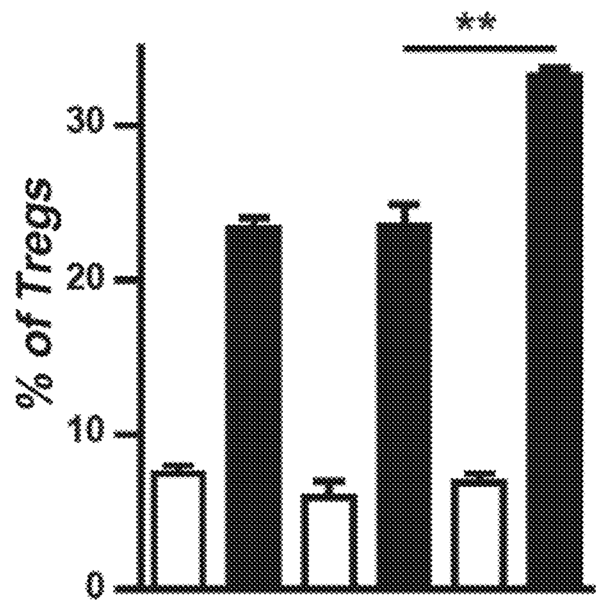
Figure 3C:
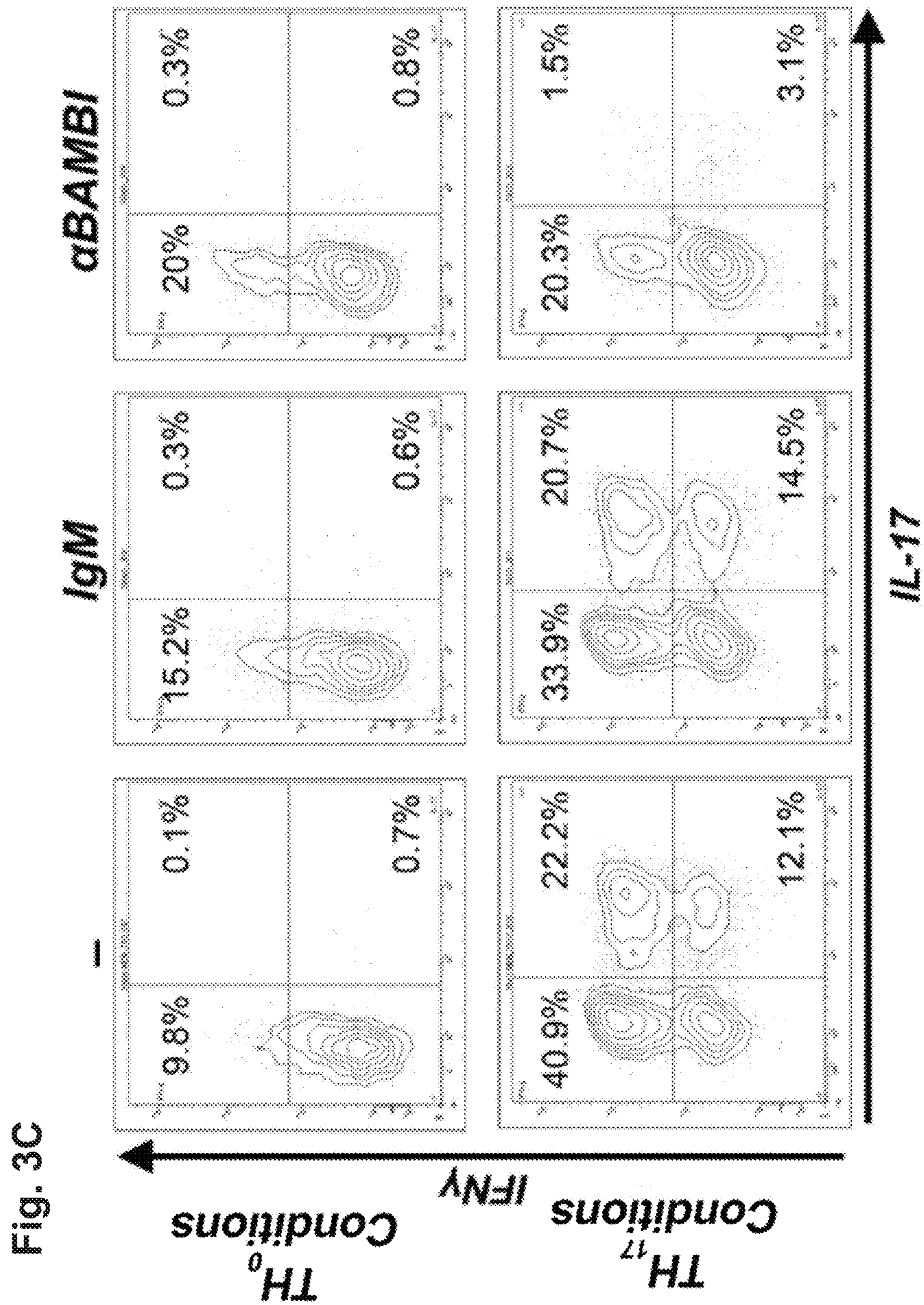

Lastly, we observed that in the presence of mAb B143-14, but not of the IgM control, the in vitro differentiation of human naïve CD4+ T lymphocytes (a Treg) or memory T lymphocytes (a Th17) activated in polarizing conditions to Treg (FIG. 3B) or TH17 (FIG. 3C) is altered in the same way as in the mouse: an increase in Treg and reduction in TH17.

Example 4: The Therapeutic Effect of mAb B101-37 in the Development of CIA, Mannan Induced Psoriatic Arthritis, Imiquimod Induced Psoriasis and DSS Colitis The previous results indicate that: 1) we have mAbs able to recognize BAMBI in mice and humans, 2) the expression of BAMBI is induced in the CD4+ T lymphocytes after the activation thereof in mice and humans; and 3) in both species the in vitro inhibition of BAMBI with a murine anti-BAMBI(109-133) mAb alters the functional differentiation of the CD4+ T lymphocytes in the same was as that described in B6.BAMBI-KO mice (increase in Treg cells and reduction of TH17 cells). These findings raise the possibility that the in vivo inhibition of BAMBI has a therapeutic effect on inflammatory/autoimmune pathologies.

In the present invention we have characterized the therapeutic potential of B101-37 in the development of CIA (the experimental model for rheumatoid arthritis most used by the scientific community), mannan induced psoriatic arthritis, imiquimod induced psoriasis (the experimental model of cutaneous psoriasis most used by the scientific community) and DSS colitis.

Figure 4A:
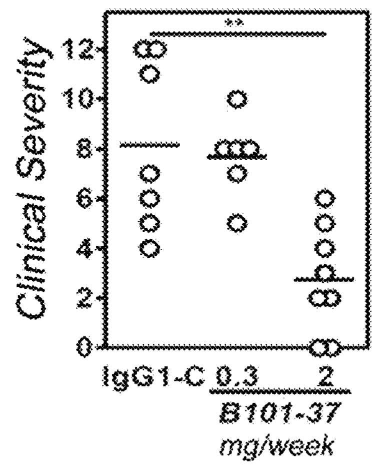
FIGS. 4A-4D illustrate MAb B101-37 inhibits the development of arthritis in the CIA model.
Figure 4B:
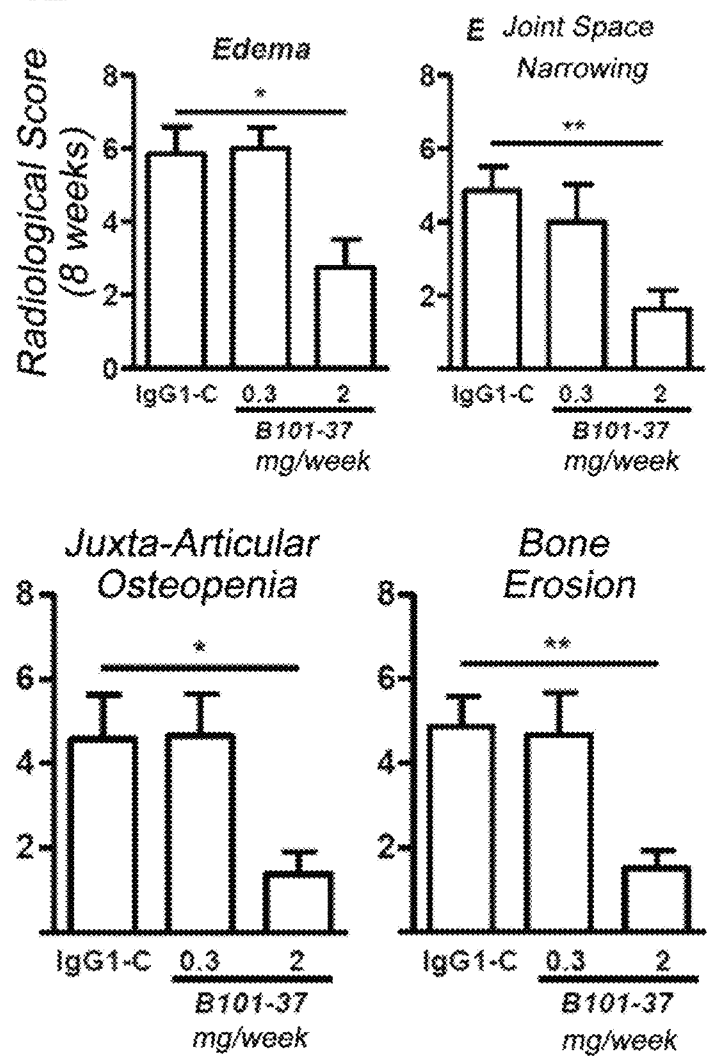
Figure 4C:
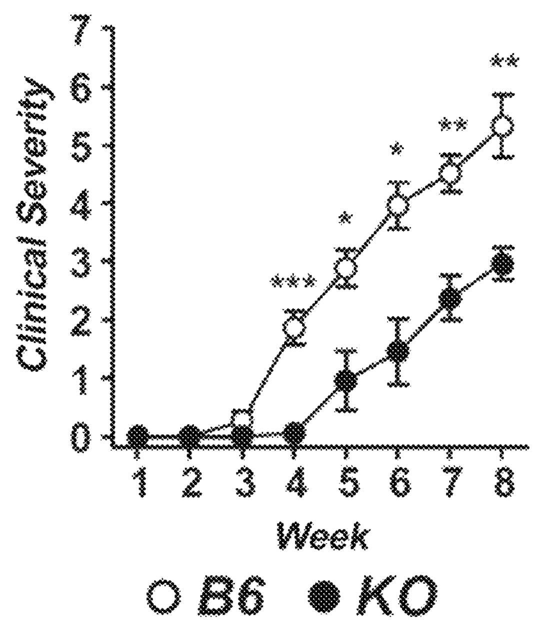
Figure 4D:
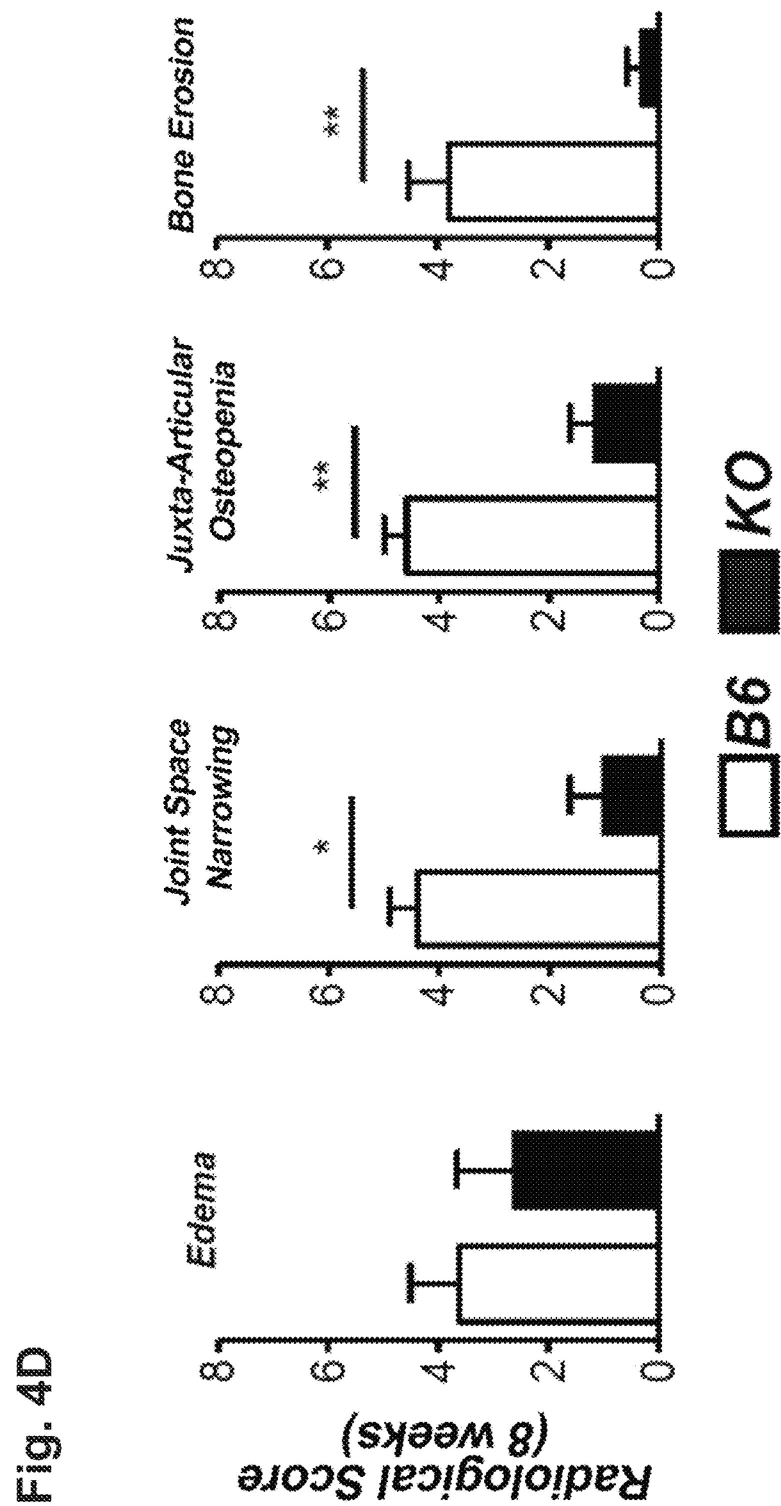

Both from a clinical and radiological point of view, the treatment of the normal B10RIII mice with 2 mg/week of B101-37 during the first 4 weeks after immunization with bovine type II collagen inhibited the development of CIA in these animals, unlike that which was observed in mice treated with 0.3 mg/week of B101-37 or with 2 mg/week of IgG1-C (FIGS. 4A and 4B). CIA inhibition after treatment with the high dose of B101-37 was similar to that observed in B10RIII.BAMBI-KO immunized mice (FIGS. 4C and 4D).

Figure 5A:
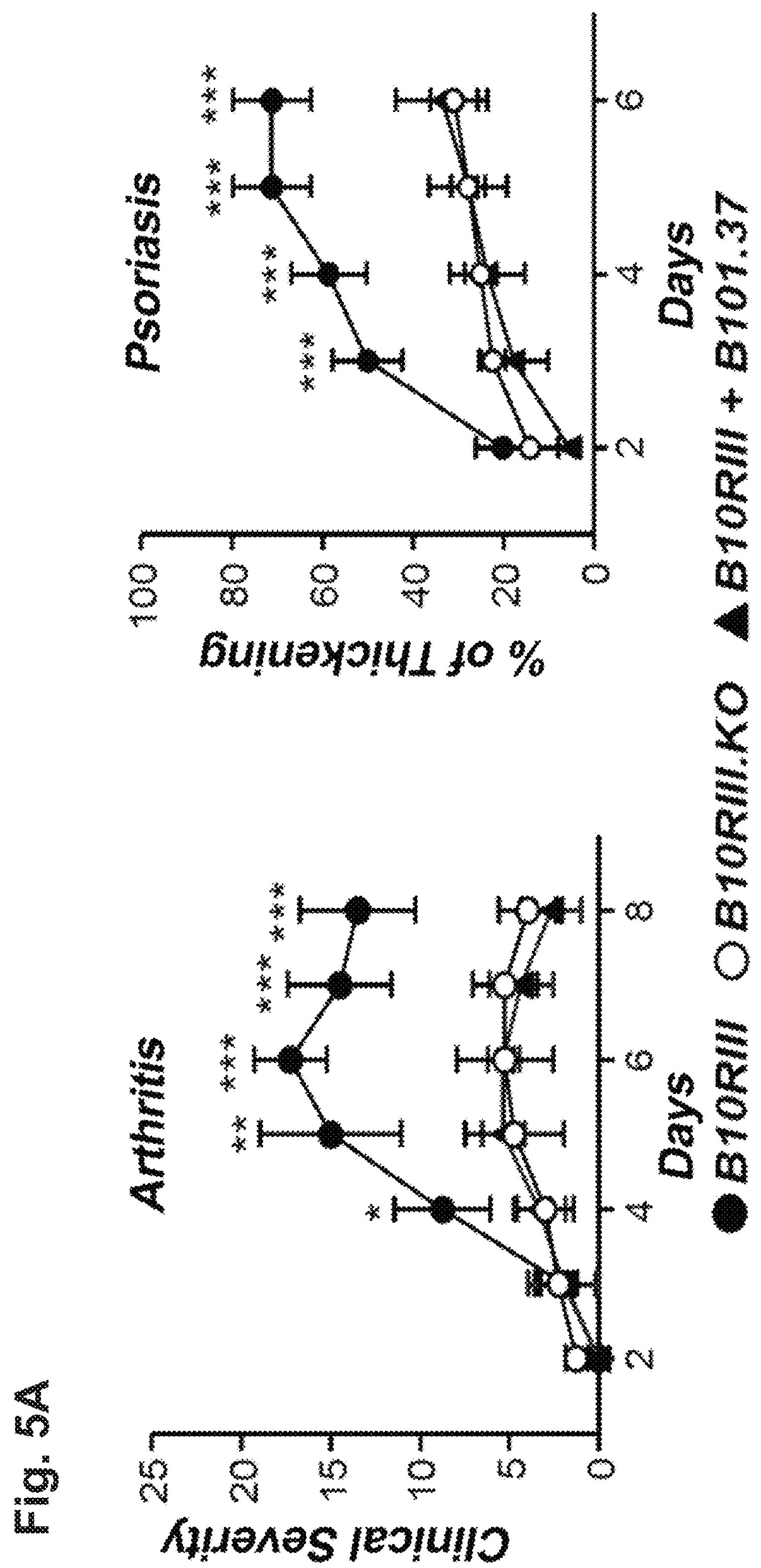
FIGS. 5A-5B illustrates the effect of the treatment with B101-37 on the development of psoriatic arthritis induced by mannan injection.
Figure 5B:
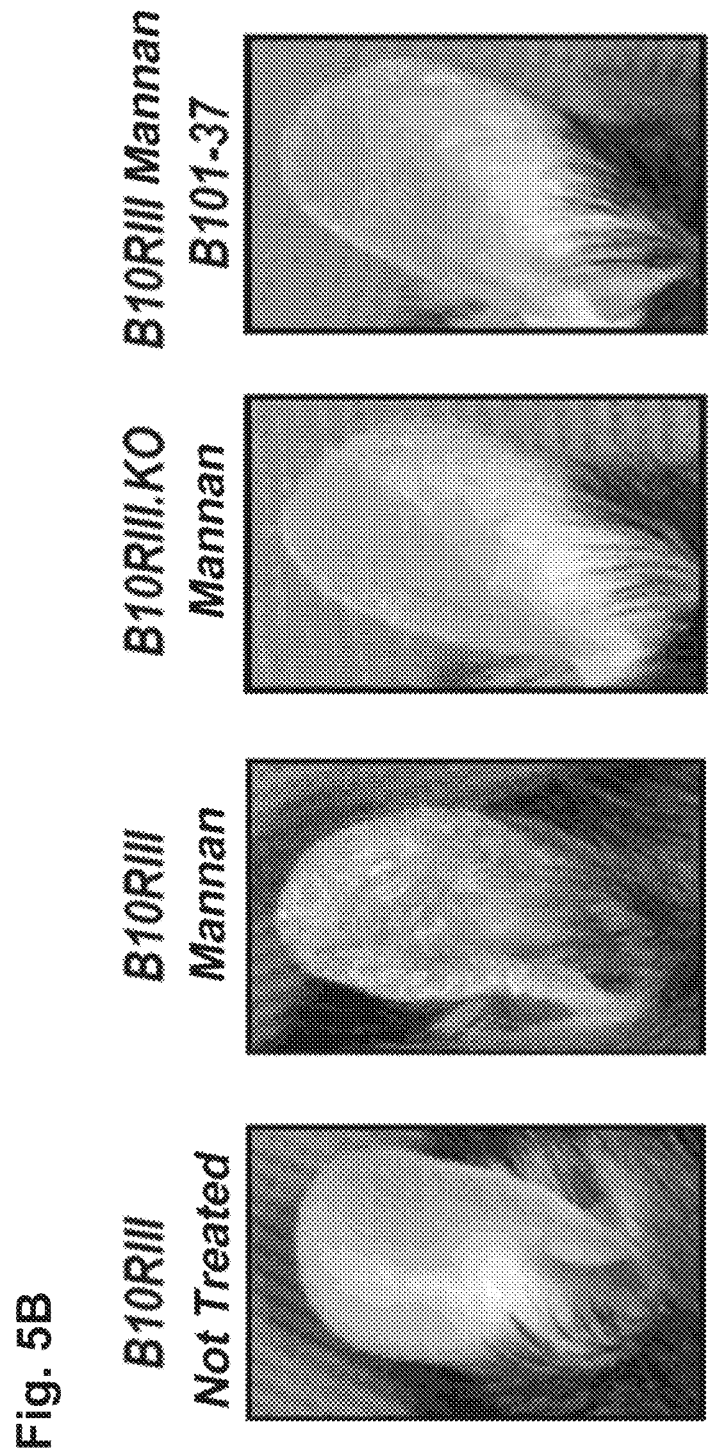

Just like the CIA model, treatment with 2 mg/week of B101-37 from the moment of mannan administration to the normal B10RIII mice reduced the severity of the articular and cutaneous legions in a highly significant way in this experimental model of acute psoriatic arthritis induced after a single mannan injection, similar to that which is observed in B10RIII.BAMBI-KO (FIGS. 5A and 5B).

Figure 6:
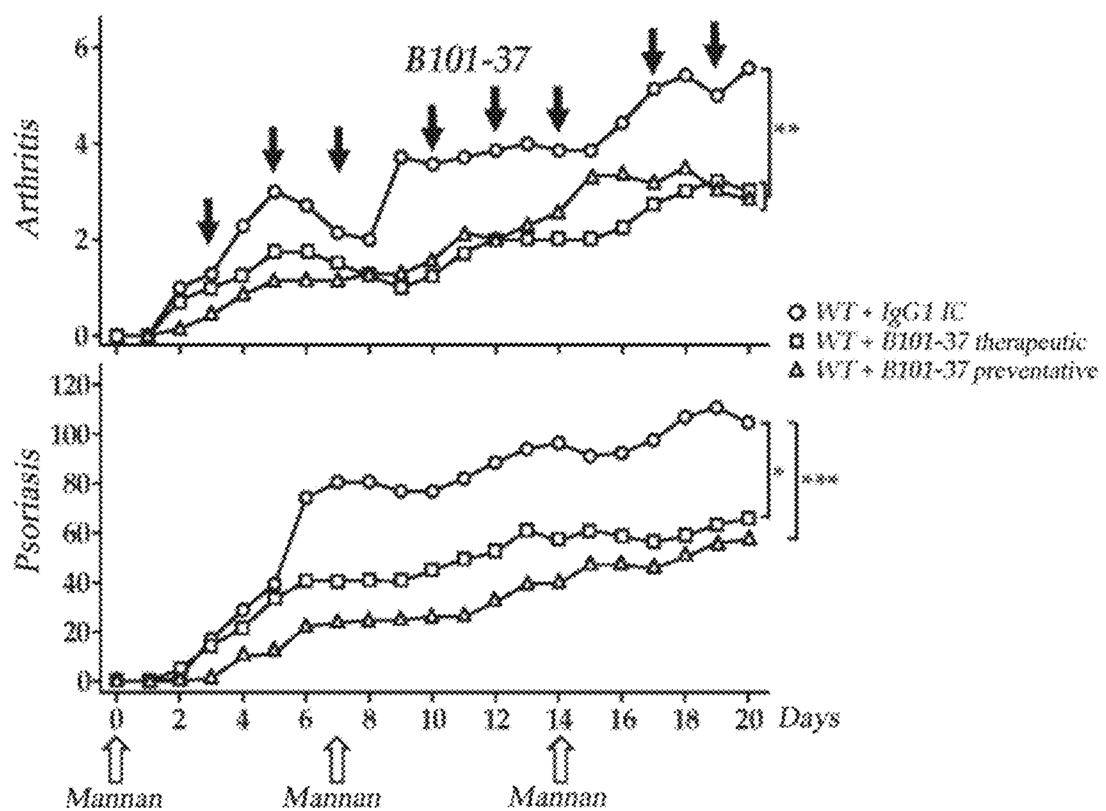
FIG. 6 illustrates therapeutic effect of treatment with B101-37 in the development of chronic psoriatic arthritis. Normal B10RIII mice received a weekly injection of 10 mg of mannan (white arrows) and were treated with mAb B101-37 (2 mg/mouse/week) from the moment of the first mannan injection (preventative B101-37) or from the appearance of the first signs of the disease (therapeutic B101-37) until the end of the experiment (black arrows). As controls, mice treated with 2 mg/mouse/week of one irrelevant murine IgG1 (IgG1-C) were used. It shows the evolution of the clinical severity of the arthritis (top panel) and the ear thickness (bottom panel) as a marker of the severity of the cutaneous psoriasis. The statistical differences are represented as: *p<0.05, p<0.01, * p<0.001.

The previous results show a preventative effect of treatment with B101-37 on the development of acute cutaneous and articular injuries after the administration of a single injection of mannan. The therapeutic potential of B101-37 in the chronic variety of this experimental model was subsequently analyzed. FIG. 6 shows that the weekly mannan injection into B10RIII mice causes the appearance of articular and cutaneous injuries that are maintained over time. Preventative treatment with 2 mg/week of B101-37 37 (begun at the moment of the mannan injection and maintained until the end of the experiment) significantly reduced the severity of said injuries throughout the study (FIG. 6). Likewise, a significant reduction, similar to that observed in preventative treatment, of the cutaneous and articular manifestations was observed after the beginning of the treatment with B101-37 once the first signs of the disease were already apparent (three days after the first mannan injection (FIG. 6).

Figure 7A:
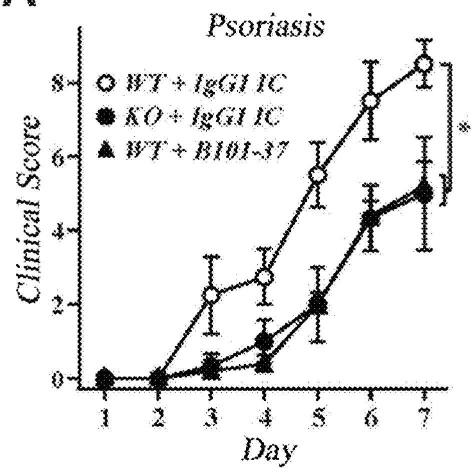
FIGS. 7A-7B illustrate the effect of treatment with B101-37 in the development of imiquimod-induced psoriasis. 12.5 mg of imiquimod (Aldara□) was applied for 6 days on the right ears of the B10RIII mice, BAMBI deficient or not. The different experimental groups were treated from the moment of the first application of imiquimod with a single dose of 2 mg of B101-37 or of irrelevant murine IgG1 (IgG1-C).
Figure 7B:
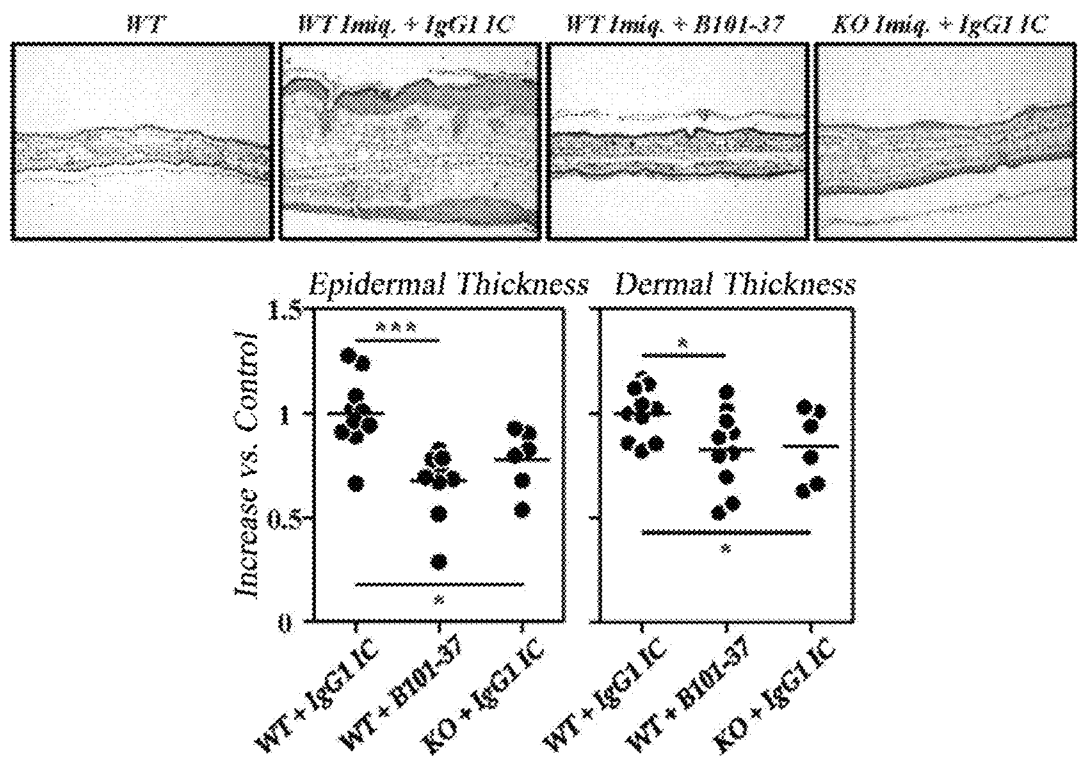

The therapeutic potential of B101-37 in psoriasis was confirmed in the cutaneous psoriasis experimental model most widely used in the scientific community, imiquimod induced psoriasis. The topical application of imiquimod for 6 consecutive days to non-transgenic B10RIII mice induces cutaneous legions with histological characteristics of psoriasis (FIGS. 7A and 7B). Unlike the previous model, the administration of imiquimod does not cause the development of arthritis. The treatment of non-transgenic B10RIII mice with B101-37, from the moment of the first application of imiquimod and with the same dose used in the preceding models, significantly reduced the severity of the disease from a clinical (FIG. 7A) and histological (FIG. 7B) point of view, as observed in B10RIII-BAMBI.KO mice.

Figure 8B:
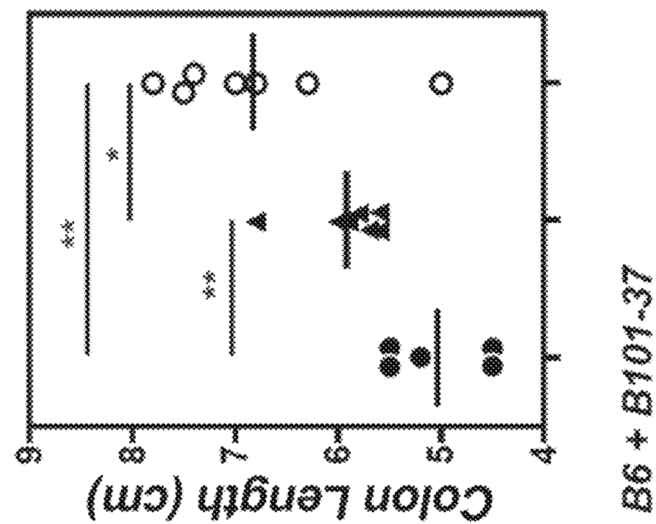
FIGS. 8A-8C illustrate the therapeutic effect of the treatment with B101-37 on the development of DSS colitis. Normal B6 or BAMBI-KO mice, treated or not from the beginning of the experiment with mAb B101-37 (2 mg/mouse/week) received DSS dissolved at a ratio of 3% in the water of the bottle for 5 days. The severity of the colitis was assessed by means of DAI quantification (FIG. 8A) or analyzing the shortening of the colon (FIG. 8B).
Figure 8A:
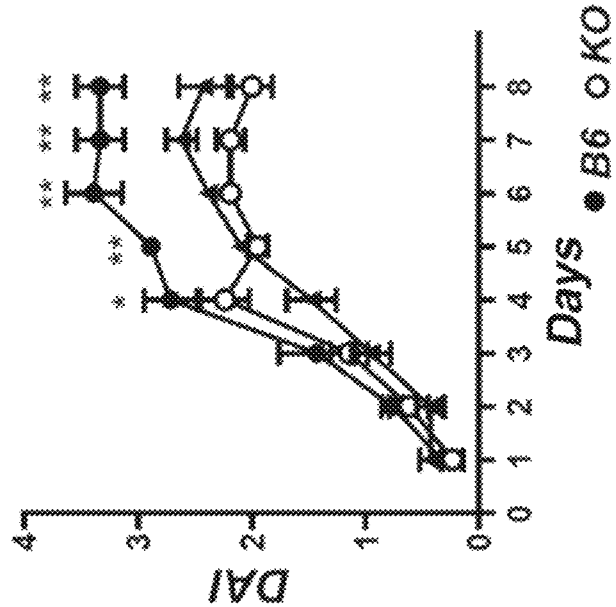
Figure 8C:
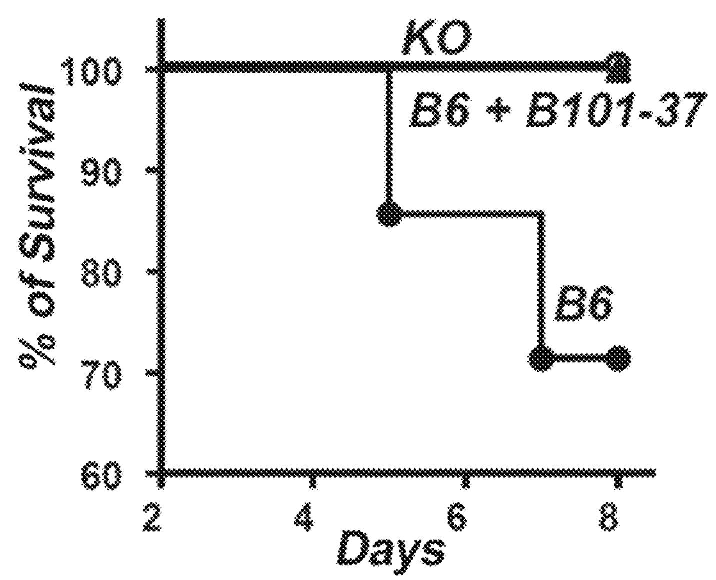

Lastly, we evaluated the therapeutic effect of B101-37 in the experimental model of DSS colitis. Just like in B6.BAMBI-KO mice, normal B6 mice treated with 2 mg/week of B101-37 from the moment of the administration of DSS developed a significantly less sever colitis than the non-treated controls (FIG. 8A). However, the protective effect of the treatment with B101-37 in B6 mice was not as important as that observed in BAMBI-KO animals, especially with regard to the degree of shortening of the colon (FIG. 8A, right panel). It is worth pointing out that both in the B6 animals treated with B1010-37 and in BAMBI-KO mice, the mortality associated with the induction of DSS colitis was entirely prevented (FIG. 8B).

Therefore, the present invention demonstrates the use of monoclonal antibodies against BAMBI for the treatment and prevention of autoimmune diseases.

The invention claimed is:

1. A monoclonal antibody, or an antigen-binding fragment thereof, that specifically recognizes the amino acid sequence of SEQ ID NO: 1 or SEQ ID NO: 2, wherein the antibody comprises a full complement of six CDRs from a heavy chain variable region and a light chain variable region respectively encoded by SEQ ID NO: 3 and by SEQ ID NO: 4, or a full complement of six CDRs from a heavy chain region and a light chain region respectively encoded by SEQ ID NO: 5 and by SEQ ID NO: 6.

2. A pharmaceutical composition comprising the antibody, or antigen-binding fragment thereof, according to claim 1.

3. A kit and/or device comprising the antibody, or antigen-binding fragment thereof, according to claim 1.

4. An antiserum that comprises the antibody, or antigen-binding fragment thereof, according to claim 1.

5. A pharmaceutical composition comprising the antiserum according to claim 4.

6. A kit and/or device comprising the antiserum according to claim 4.

7. A method of treating an autoimmune disease in a subject, comprising administering to the subject in need thereof an effective amount of the antibody, or antigen-binding fragment thereof, according to claim 1, wherein the autoimmune disease is selected from the group consisting of rheumatoid arthritis, spondyloarthritis, psoriasis, systemic lupus erythematosus, and inflammatory bowel disease.

* * * * *

SEQUENCE LISTING

<160> NUMBER OF SEQ ID NOS: 11

<210> SEQ ID NO 1
<211> LENGTH: 25
<212> TYPE: PRT
<213> ORGANISM: Artificial Sequence
<220> FEATURE:
<223> OTHER INFORMATION: murine BAMBI (109-133) peptide

<400> SEQUENCE: 1

Leu His Asp Val Leu Ser Pro Ser Lys Ser Glu Ala Ser Gly Gln Gly
1               5                   10                  15

Asn Arg Tyr Gln His Asp Ser Ser Arg
            20                  25

<210> SEQ ID NO 2
<211> LENGTH: 25
<212> TYPE: PRT
<213> ORGANISM: Artificial Sequence
<220> FEATURE:
<223> OTHER INFORMATION: Human BAMBI (109-133) peptide

<400> SEQUENCE: 2

Leu His Asp Val Leu Ser Pro Pro Arg Gly Glu Ala Ser Gly Gln Gly
1               5                   10                  15

Asn Arg Tyr Gln His Asp Gly Ser Arg
            20                  25

<210> SEQ ID NO 3
<211> LENGTH: 396
<212> TYPE: DNA
<213> ORGANISM: Artificial Sequence
<220> FEATURE:
<223> OTHER INFORMATION: mAb B101-37 heavy chain

<400> SEQUENCE: 3
cagctggagc agtcaggacc tgagctgaag aggcctggag agacagtcaa gttctcctgc     60
aaggcttctg ggtatccctt cacaaactat ggaatgcact gggtgaaaca ggctccagga    120
aagggtttaa agtggatggg ctggataaac acccacactg gagagccaac atatgctgat    180
gacttcaggg gacggtttgc cttctctttg gaaacctctg ccagcactgc ctatttgcag    240
atcaacaacc tcaaaaatga ggacacggct acatatttct gtgcaagaga gggttattat    300
aactacgaag gctggtactt cgatgtctgg ggcgcaggga ccacggtcac cgtctcctca    360
gccaaaacga cacccccatc tgtctataga tcttcc                              396

<210> SEQ ID NO 4
<211> LENGTH: 365
<212> TYPE: DNA
<213> ORGANISM: Artificial Sequence
<220> FEATURE:
<223> OTHER INFORMATION: mAbB 101-37 light chain

<400> SEQUENCE: 4
gggagctcga cattgtgctg acccagtctc catccagtct gtctgcatcc cttggagaca     60
caattaccat cacttgccat gccagtcaga acatttattt ttggttaagt tggtaccagc    120
agaaaccagg aaatattcct aaactattga tctataaggc ttccaacttg cacacaggcg    180
tcccatcaag gtttagtggc agtggatctg gaacaggttt cacattaacc atcagcagcc    240
tgcagcctga agacattgcc acttactact gtcaacaggg tcaaagttat ccgctcacgt    300
tcggtgctgg gaccaagctg gagctgaaac gggctgatgc tgcaccaact gtatccgcat    360

```
gcacc                                                              365


<210> SEQ ID NO 5
<211> LENGTH: 384
<212> TYPE: DNA
<213> ORGANISM: Artificial Sequence
<220> FEATURE:
<223> OTHER INFORMATION: mAb B143-14 heavy chain

<400> SEQUENCE: 5

cttccggaat tccaagttca gctggaggag tcaggggctg agcttgtgaa gcctggggct    60

tcagtgaaga tgtcctgcaa ggcttctggc tacaccttca ccagctactg gataaactgg   120

gtgaagctga ggcctggaca aggccttgag tggattggag atatttatcc tggtagtggt   180

agtactaact acaatgagaa gttcaagagc aaggccacac tgactgtaga cacatcctcc   240

agcacagcct acatgcaact cagcagcctg acatctgagg actctgcggt ctattactgt   300

gcaactgggt ttgactactg gggccaaggc accactctca cagtctcctc agagagtcag   360

tccttcccaa atgtcagatc ttcc                                          384


<210> SEQ ID NO 6
<211> LENGTH: 362
<212> TYPE: DNA
<213> ORGANISM: Artificial Sequence
<220> FEATURE:
<223> OTHER INFORMATION: mAb 143-14 light chain

<400> SEQUENCE: 6

gggagctcga cattgtgctc acccagtctc cagccaccct gtctgtgact ccaggagata    60

gcgtcagtct ttcctgcagg gccagccaaa gtattagcaa caacctacac tggtatcaac   120

aaaaatcaca tgagtctcca aggcttctca tcaagtatgc ttcccagtcc atctctggga   180

tcccctccag gttcagtggc agtggatcag ggacagattt cactctcagt atcaacagtg   240

tggagactga agattttgga atgtatttct gtcaacagag taacagctgg tggacgttcg   300

gtggaggcac caagctggaa atcaaacggg ctgatgctgc accaactgta tccgcatgca   360

cc                                                                  362


<210> SEQ ID NO 7
<211> LENGTH: 32
<212> TYPE: DNA
<213> ORGANISM: Artificial Sequence
<220> FEATURE:
<223> OTHER INFORMATION: degenerate amplicon 5' from the FR1 of the
      heavy chain
<220> FEATURE:
<221> NAME/KEY: misc_feature
<222> LOCATION: (18)..(18)
<223> OTHER INFORMATION: n is a, c, g, or t

<400> SEQUENCE: 7

cttccggaat tcsargtnma gctgsagsag tc                                  32


<210> SEQ ID NO 8
<211> LENGTH: 36
<212> TYPE: DNA
<213> ORGANISM: Artificial Sequence
<220> FEATURE:
<223> OTHER INFORMATION: amplicon 3' of the constant region of IgG1

<400> SEQUENCE: 8

ggaagatcta tagacagatg gggtgtcgt tttggc                               36
```

-continued

```
<210> SEQ ID NO 9
<211> LENGTH: 33
<212> TYPE: DNA
<213> ORGANISM: Artificial Sequence
<220> FEATURE:
<223> OTHER INFORMATION: amplicon 3' of the constant region of IgM

<400> SEQUENCE: 9

ggaagatctg acatttggga aggactgact ctc                               33


<210> SEQ ID NO 10
<211> LENGTH: 32
<212> TYPE: DNA
<213> ORGANISM: Artificial Sequence
<220> FEATURE:
<223> OTHER INFORMATION: degenerate amplicon from the FR1 of the light
      chain kappa

<400> SEQUENCE: 10

gggagctcga tattgtgmts acmcarwctm ca                                32


<210> SEQ ID NO 11
<211> LENGTH: 30
<212> TYPE: DNA
<213> ORGANISM: Artificial Sequence
<220> FEATURE:
<223> OTHER INFORMATION: amplicon 3' from the constant region of the
      light chain kappa

<400> SEQUENCE: 11

ggtgcatgcg gatacagttg gtgcagcatc                                   30
```